United States Patent
Olstein et al.

(10) Patent No.: US 7,034,113 B2
(45) Date of Patent: Apr. 25, 2006

(54) BACTERIOCIN-METAL COMPLEXES IN THE DETECTION OF PATHOGENS AND OTHER BIOLOGICAL ANALYTES

(75) Inventors: Alan D. Olstein, Mendota Heights, MN (US); Joellen Feirtag, St. Paul, MN (US)

(73) Assignee: Paradigm Diagnostics, LLC, Mendota Heights, MN (US)

( * ) Notice: Subject to any disclaimer, the term of this patent is extended or adjusted under 35 U.S.C. 154(b) by 164 days.

(21) Appl. No.: 10/082,618

(22) Filed: Feb. 22, 2002

(65) Prior Publication Data

US 2003/0175207 A1 Sep. 18, 2003

(51) Int. Cl.
C07K 14/00 (2006.01)
A61B 5/00 (2006.01)
C12Q 1/00 (2006.01)

(52) U.S. Cl. .......................... 530/350; 530/400; 435/4; 424/9.6

(58) Field of Classification Search ................ 424/44, 424/93.1, 9.6; 426/56, 63, 106, 335, 532; 530/300, 350, 403; 435/6, 7.1, 7.2, 7.92, 435/287.1, 287.2, 4; 536/25.32; 436/532, 436/542, 543, 544, 545, 546, 56, 57, 164, 436/172, 1
See application file for complete search history.

(56) References Cited

U.S. PATENT DOCUMENTS 5,541,113 A * 7/1996 Siddigi et al.
5,691,301 A 11/1997 Blackburn et al.
5,750,357 A * 5/1998 Olstein et al.
6,287,617 B1 9/2001 Bender et al.

FOREIGN PATENT DOCUMENTS

EP 0659068 * 4/1996
WO WO 96/16180 * 5/1996
WO WO 14/27628 4/2001

OTHER PUBLICATIONS

Pommer et al., Journal of Biological Chemistry, vol. 274(38), pp. 27153-27160 (1999).*
Carey, Francis A, Organic Chemistry, Fourth Ed., McGraw-Hill Higher Education, 2000 (Periodic Table from Back inside cov r).*
Isacsson et al., Analytica Chimica Acta, 68: 339-62 (1974).*
Bowi et al., Science, vol. 247, pp. 13006-1310 (1990).*
Friedman, M., Journal of Agricultural and Food Chemistry, vol. 47 No. 4, pp. 1295-319 (Apr. 1999).*
Buchman et al, Journal of Biological Chemistry, vol. 263 No. 31, pp. 16260-66 (1988).*
NCBI Protein Accession AAA88606, nisin.*
NCBI Nucleotide, Accession J04057, S. Lactis antibiotic nisin (spaN) gene, complete cds.*
Surovoy et al., Peptides 1992, Proceedings of hte European Peptide Symposium, 22nd (a993), Meeting date 1992, pp. 563-564, ESCOM (Pub.), Leiden, Neth.*
Pearce et al., Journal of Agricultural and Food Chemistry, vol. 36, pp. 707-717 (1988).*
Weber OA, International Journal of Protein Research, vol. 3 No. 5, pp. 255-259 (1971).*
Jung et al., Angewandte Chemie, Interantional English Edition, vol. 30 No. 9, pp. 1051-1068 (19910.*
Fratamico et al. (1992), "Rapid Isolation of *Escherichia coli* O157:H7 From Enrichment Cultures of Foods Using an Immunomagnetic Separation Method," *Food Microbiol.* 9:105-113.
Kricka, et al. (1983), "Chemiluminescent and Bioluminescent Methods in Analytical Chemistry," *Analyst* 108:1274-1296.
Nissen-Meyer et al. (1997), "Ribosomally Synthesized Antimicrobial Peptides: Their Function, Structure, Biogenesis, and Mechanism of Action," *Archives of Microbiology* 167(2+3):67-77.
Pyle et al. (1999), "Sensitive Detection of *Escherichia coli* O157:H7 in Food and Water by Immunomagnetic Separation and Solid-Phase Laser Cytometry," *Appl. Environm. Microbiol.* 65(5):1966-1972.
Restaino et al. (1997), "A 5-h Screening and 24-h Confirmation Procedure for Detecting *Escherichia coli* O157:H7 in Beef Using Direct Epiflourescent Microscopy and Immunomagnetic Separation," *Letters in Applied Microbiology* 24:401-404.

(Continued)

*Primary Examiner*—James C Housel
*Assistant Examiner*—Zachariah Lucas
(74) *Attorney, Agent, or Firm*—Joseph T. Leone, Esq.; DeWitt Ross & Stevens S.C.

(57) ABSTRACT

Complexes of bacteriocins and metals are provided that are useful in detecting bacteria, fungi and other biological analytes, and are particularly useful in detecting gram positive bacteria. The complexes are preferably chelated complexes wherein the bacteriocin is a lantibiotic, non-lanthionine containing peptide, large heat labile protein and complex bacteriocin, fusion protein thereof, mixture thereof, and fragment, homolog and variant thereof, and (b) a detectable label comprising a transition or lanthanide metal. The complex preferentially binds to viable gram positive or mycobacterial cells. The complex can also bind to gram negative bacteria and fungi. Methods of using the complexes in assays, diagnosis and imaging are also provided.

14 Claims, 3 Drawing Sheets

OTHER PUBLICATIONS

Rost et al. (1998), "What Do We Measure with Luminol-, Lucigenin- and Penicillin-Amplified Chemiluminescence? 1. Investigations with Hydrogen Peroxide and Sodium Hypochlorite," *J. Biolumin. Chemilumin. 13*:355-363.

Sahl et al. (1998), "Lantibiotics: Biosynthesis and Biological Activities of Uniquely Modified Peptides from Gram-Positive Bacteria," *Annu. Rev. Microbiol. 52*:41-79.

* cited by examiner

Abu = α-aminobutyric acid
Dha = dehydroalanine
Dhb = dehydrobutyrine

BACTERIOCIN-METAL COMPLEXES IN THE DETECTION OF PATHOGENS AND OTHER BIOLOGICAL ANALYTES

FIELD OF THE INVENTION

The invention relates generally to detection of biological analytes, and more particularly relates to novel complexes of bacteriocins and metals useful in the catalytic detection of gram-positive bacteria, gram-negative bacteria, mycobacteria, fungi and other biological analytes.

BACKGROUND

The risk from pathogenic microorganisms in foods has been recognized for many years, and bacterial agents are generally implicated as the contaminants. Food-borne disease may be one of the most notable public health problems. The rapid detection and identification of pathogenic microorganisms in foods, and its manufacturing environment, is of utmost importance if we are to develop and implement control and prevention strategies leading to a safer food supply. From 1993–1997, 2,751 outbreaks of food-borne illness were reported to the CDC. These outbreaks accounted for 86,058 persons affected. Bacterial pathogens caused the largest percentage (75%) of these reported outbreaks. The predominant cause in the reported cases was *Salmonella Enteritidis*, thought to have originated in egg products. Additionally, multi-state outbreaks of *Eschericia coli* 0157:H7 contributed significantly to the total figures for morbidity and mortality (1). *Listeria monocytogenes*, a gram-positive contaminant, is an emerging public health threat to the safety of food products as well.

In addition to issues related to food safety, antibiotic-resistant bacteria, including Gram-positive bacteria, are becoming an increasing issue in U.S. hospitals and communities. Community-acquired pneumonia strikes approximately four million Americans each year and hospitalizes about 600,000. Approximately 500,000 cases of community-acquired pneumonia each year are the result of infection with *S. pneumoniae*, as shown in the New England Journal of Medicine (1995; 333:1618–1624). Resistance to penicillin, the most common agent used to treat *S. pneumoniae*, now approaches 40 percent. Additional resistance has been reported against cephalosporins and non-beta-lactam agents, and nearly half of these strains can be classified as highly resistant. High-dose penicillin and cephalosporins remain first-line therapies, however, a broader range of agents is needed. Vancomycin, the next generation of fluoroquinolones with agents such as sparfloxacin, the new streptogramin class, as well as combination therapies, will help physicians stay one step ahead of resistant pneumococci.

The gram-positive pathogens, penicillin-resistant *Streptococcus pneumoniae*, methicillin-resistant *Staphylococcus aureus* and vancomycin-resistant enterococci, complicate the treatment of serious infections and have been linked to extended hospitalizations, higher medical costs and high mortality rates. Drug-resistant *Streptococcus pneumoniae* poses a growing threat to people in places where they live and work. *Streptococcus pneumoniae* infections—including pneumonia, sinusitis, meningitis and otitis media—are among the leading causes of death and illness among the elderly, young children and persons with underlying medical conditions. Drug-resistant *S. pneumoniae* often strikes vulnerable patient populations in daycare settings, nursing homes and prisons.

*Staphylococcus aureus*, the most common cause of more than a dozen conditions in both hospitals and communities, often colonizes without any sign of infection, and then from this reservoir gains access to skin and deep tissue, where it subverts the immune system. Staphylococcal infections range from local skin infections to endocarditis (heart valve infection), osteomyelitis (bone infection) and sepsis (blood stream infection). Methicillin-resistant *S. aureus* first emerged in the early 1960s. Several strains of *S. aureus* are now resistant to a wide variety of currently available antibiotics, including penicillins, macrolides, fluoroquinolones and lincosamides.

In the same bacteria family, multidrug-resistant *Staphylococcus epidermidis* also compromises patient health, and has been established as a leading cause of hospital-acquired bloodstream infections. More than 80 percent of *S. epidermidis* isolates in U.S. hospitals are methicillin resistant, and recent studies have found resistance to quinolones, cephalosporins and vancomycin. This drug resistance is a growing concern, particularly for immunocompromised cancer patients.

Vancomycin is considered the agent of last resort for Gram-positive infections. Vancomycin-resistant enterococci, an increasingly frequent cause of hospital-acquired infections in the United States, are resistant to virtually all currently available antibiotics including vancomycin.

Accordingly, there is a significant need in the art for an effective method of detecting and diagnosing these pathogens. Unfortunately, to date, testing bacteria, yeast and fungi has been excessively time consuming and labor intensive. While the onset of symptoms from endotoxin from coliform bacteria may be exceedingly rapid, laboratory based diagnosis will typically take days. The present techniques used to detect the presence of bacteria involve aseptic transfer of a sample, streaking the sample having bacterial organisms on agar plates after serial dilution, and colony enumeration. This laborious and lengthy process requires at least 24 to 48 hours for a positive result and substantially longer for a negative result.

Both the detection and characterization of microbial contaminants in food and water samples have historically relied upon the use of bacterial enumeration techniques, both in liquid and solid culture media. These methods, while sufficiently sensitive to detect a small number of viable organisms, require lengthy sample preparation time. The use of ELISA techniques and nucleic acid hybridization probes, while accurate, have less sensitivity, and therefore require lengthy isolation and enrichment periods to reach the analytical detection limits for these techniques. Therefore, there is a need for a method of determining cell numbers that is fast as well as sensitive.

Other analyte tests require an organism to ingest a detectable material, such as fluorescein. In yet other tests, an antibody, specific for an antigen on the target bacteria is labeled with fluorescein to make a fluorescent antibody. Another approach involves use of a visualization polymer coupled to a detecting agent that binds the target organism, wherein the visualization polymer is made up of detectable visualization units, such as multiple enzymes or labeled polyolefins, which are directly or indirectly bonded together (see, e.g., U.S. Pat. No. 4,687,732 to Ward et al.). Another approach involves covalent conjugation of polymyxin B (PMB) and an enzyme reporter molecule, such as horseradish peroxidase (HRP), to produce a complex for use in a binding assay to detect the target organism (Applemelk et al. (1992) *Anal. Biochem.* 207:311–316). An organic "chemical tag" that comprises populations of binding agents and detectable labels has also been described (Olstein et al., U.S. Pat. No. 5,750,357).

However, all of the aforementioned labeling methods suffer from the inherent steric interference introduced by the size of the tag, typically larger than 100 $D^3$, primarily contributed by the reporter group, usually an enzyme. By contrast, the antibiotic usually being a substantially smaller molecule (20 $D^3$) than the macro-molecular complexes described above, can readily penetrate membrane-bound receptors on the cell surface. Consequently, a continuing need exists for a sensitive and rapid method to detect extremely small amounts of target biological analytes.

Antibiotics have been used primarily as therapeutic agents and growth promoting substances. However, there is evidence in the literature for their use for diagnostic purposes (2,3). Many methods for conjugation of reporter groups to antibiotic compounds are frequently unsuitable, for both technical reasons, such as loss of biological activity, loss of solubility and economic, i.e. the cost of enzymes, dyes and the conjugation chemistry. Chemiluminescent labeling of macromolecules has been demonstrated to yield greater analytical sensitivity than the use of many fluorescent probes because of simplicity of the optics resulting in lower background signal (4).

Therefore, there is a need in the art for detection methods for pathogenic organisms. Ideal methods would utilize small reporter groups and provide sensitive detection. There is a further need to preferentially detect viable organisms, as non-viable organisms may not of themselves provide a threat to the health of an individual and may not indicate the source of any potential danger, particularly where bacteria are a food contaminant. Further, there is a need to distinguish over any background signal of non-viable pathogens in order to accurately determine the numbers of live cells.

SUMMARY OF THE INVENTION

Accordingly, it is an object of the present invention to provide methods for sensitive and rapid detection of bacteria and other pathogens. The present invention is directed to a novel bacteriocin derivative that takes the form of a chelated complex comprising a bacteriocin and a metal. The chelated complexes are useful as bacterial probes having sensitive detection and being capable of detecting low cell numbers. The complexes are also useful to study the development of antibiotic resistance.

The chelated complexes of the present invention are comprised of (a) a bacteriocin selected from the group consisting of lantibiotics, non-lanthionine containing peptides, large heat labile proteins and complex bacteriocins, fusion proteins thereof, mixtures thereof, and fragments, homologs and variants thereof, and (b) a detectable label comprising a transition or lanthanide metal. The complexes bind to gram positive bacteria or mycobacteria cells. Permeabilized gram negative bacteria cells and fungi may also be tested.

Useful transition metals are Cu, Co, Fe, Mn, Cr, Ni, Zn, Tc, and their isotopes. Lanthanide metals may also be used, such as Gd, La, Eu, Tb, Dy, and Er. A preferred metal is Cr. An especially preferred metal is Co.

Preferred bacteriocins are the lantibiotics, such as nisin, mutacin, subtilin, gallidermin, Pep5, epicidin 280, epilancin K7, lactocin S, streptococcin A-FF22, lacticin 481, salivaricin A, variacin, cypemycin, mersacidin, cinnamycin, duramycin and ancovenin, actagardine, sublancin, plantaricin C, fusion proteins thereof, mixtures thereof and fragments, homologs and variants thereof. An especially preferred lantibiotic is nisin.

Non-lantibiotic bacteriocins, such as plantaricin, thermophilin and mesentericin Y, may also be useful. Any of the ribosomally synthesized cationic defense proteins that bind to the membranes of target bacteria are included within the present claims.

The invention also includes a method for synthesizing a bactenocin-metal complex, comprising: (a) admixing (i) a water soluble salt of metal selected from the group consisting of transition metals and lanthanides with (ii) a bacteriocin selected from the group consisting of lantibiotics, non-lanthionine containing peptides, large heat labile proteins and complex bactenocins, fusion proteins thereof, mixtures thereof, and fragments, homologs and variants thereof in (iii) a solvent for the metal salt and the bacteriocin, wherein the admixing is conducted under conditions effective to promote chelation of the metal by the bacteriocin, thereby forming a solution of the complex of the bacteriocin and the metal; (b) desalting the complex; and (c) isolating and drying the complex. A particular advantage of these complexes is their ability to bind to viable cells, but not to nonviable cells, which allows the bacteriocin metal complexes to distinguish between viable cells and non-viable cells or cellular debris.

The invention also includes a method for forming a bacteriocin-metal complex in situ in or on a sample to be tested, comprising: (a) applying to a sample to be tested (i) a water soluble salt of metal selected from the group consisting of transition metals and lanthanides and (ii) a bacteriocin selected from the group consisting of lantibiotics, non-lanthionine containing peptides, large heat labile proteins and complex bacteriocins, fusion proteins thereof, mixtures thereof, and fragments, homologs and variants thereof, in (iii) a solvent for the metal salt and the bacteriocin, wherein the conditions are effective to promote binding of the bacteriocin-metal complex to a target pathogen.

When the bacteriocin-metal complex is allowed to bind to pathogens in situ in or on a sample, a portion of the pathogens present with the bound bacteriocin-metal complex is preferably removed for detection of pathogens, for example, by washing or using a swab or sponge. If using a swab, any pathogens that are present in or on the sample are removed from the swab and suspended in aqueous buffer solution. The number of organisms present in the buffer is determined by measuring the luminescence in the presence of an oxidizable substrate (e.g., luminol) and a source of peroxide.

The volume of buffer containing pathogens may be concentrated if desired. Adsorptive particles (e.g. magnetic immuno-microbeads or phage-microbeads) may be used to concentrate the sample containing pathogens. Alternatively the sample may be concentrated using centrifugation or filtration.

The invention further provides a diagnostic test for conducting a chemiluminescent assay of viable bacteria, comprising a bacteriocin-metal complex, a source of peroxide and an oxidizable substrate. The oxidizable substrate may be selected from the group of chemiluminescent substrates consisting of luminol and its derivatives, lucigenin, penicillin, luciferin and other polyaromatic phthalylhydrazides. The source of peroxide is exogenous addition of hydrogen peroxide, or optionally benzoyl peroxide or cumyl peroxide, or may be an enzyme such as glucose or amino acid oxidase.

The bacteriocin-metal complex is preferably formed in situ in or on the sample to be tested using the components of the diagnostic test.

The invention further provides a method for conducting a chemiluminescent assay of pathogens comprising (a) contacting a sample with a bacteriocin-metal complex, (b) optionally washing off unbound complex and (c) detecting labeled cells by admixing a source of peroxide and an oxidizable substrate. The pathogens may be isolated from the sample prior to contacting the sample with the bacteriocin-metal complex. One method for isolating pathogens from the sample is using antibody-attached micro-beads or phage-attached microbeads consisting of polystyrene or other synthetic latex, polymer coated ferrite or super-paramagnetic materials, silica micro-beads or cross-linked polysaccharide micro-beads. The labeled cells may be combined with peroxide with an oxidizable substrate, and the light emission detected in a photodetector. Preferred peroxides are selected from the group consisting of hydrogen peroxide, benzoyl peroxide and cumyl peroxide. Preferred oxidizable substrates are luminol and its derivatives, lucigenin, penicillin, luciferin and other polyaromatic phthalylhydrazides.

The invention also includes a therapeutic treatment comprising a bacteriocin-metal chelated complex comprised of (a) a bacteriocin selected from the group consisting of lantibiotics, non-lanthionine containing peptides, large heat labile proteins and complex bacteriocins, fusion proteins thereof, mixtures thereof, and fragments, homologs and variants thereof, and (b) a detectable label comprising a transition or lanthanide metal, wherein injured or diseased tissue is treated with the bacteriocin-metal complex. A preferred transition metal is cobalt. A preferred lantibiotic is nisin.

The invention also includes a therapeutic treatment comprising a bacteriocin-metal chelated complex comprised of (a) a bacteriocin selected from the group consisting of lantibiotics, non-lanthionine containing peptides, large heat labile proteins and complex bacteriocins, fusion proteins thereof, mixtures thereof, and fragments, homologs and variants thereof, and (b) a detectable label comprising a transition or lanthanide metal, wherein injured or diseased tissue is treated with the bacteriocin-metal complex. A preferred transition metal is cobalt. A preferred lantibiotic is nisin.

The preferred bacterial target cells are selected from the group consisting of pneumococci, streptococci, staphylococci, enterococci, aerobic bacilli, pediococci, leuconostocs, anaerobic clostridia, listeria and nocardia. The complexes of the invention may also be used to detect mycobacteria, including but not limited to *mycobacterium tuberculosis, mycobacterium avium, mycobacterium paratuberculosis, mycobacterium bovis* and *mycobacterium leprae*.

In preferred embodiments, the lantibiotic is selected from the group consisting of nisin, mutacin, subtilin, gallidermin, Pep5, epicidin 280, epilancin K7, lactocin S, streptococcin A-FF22, lacticin 481, salivaricin A, variacin, cypemycin, mersacidin, cinnamycin, duramycin and ancovenin, actagardine, sublancin, plantaricin C, fusion proteins thereof, mixtures thereof, and fragments, homologs and variants thereof, the transition metal is selected from the group consisting of Cu, Co, Fe, Mn, Cr, Ni, Zn, Tc, and their isotopes, and the lanthanide metal is selected from the group consisting of Gd, La, Eu, Tb, Dy, and Er, and their isotopes.

DETAILED DESCRIPTION OF THE INVENTION

I. Definitions and Overview

Figure 1:
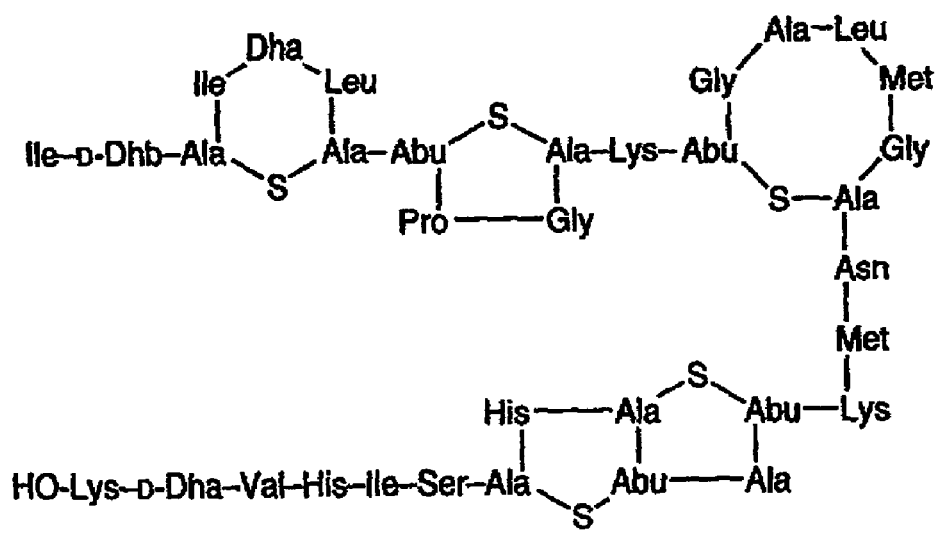
FIG. 1 illustrates the molecular structure of the lantibiotic, nisin.

Before the present invention is described in detail, it is to be understood that unless otherwise indicated this invention is not limited to specific bacteriocins, metals, ligands or the like, as such may vary. It is also to be understood that the terminology used herein is for the purpose of describing particular embodiments only and is not intended to limit the scope of the present invention.

It must be noted that as used herein and in the claims, the singular forms "a," "and" and "the" include plural referents unless the context clearly dictates otherwise. Thus, for example, reference to "a bacteriocin" includes a single bacteriocin as well as two or more bacteriocins, reference to "a complex" includes a single complex or two or more complexes, and so forth.

"Optional" or "optionally" means that the subsequently described circumstance may or may not occur, so that the description includes instances where the circumstance occurs and instances where it does not. For example, recitation of a chemical modification as "optional" encompasses both the compound as chemically modified and the unmodified compound.

The term "fragment" refers to a portion of a bacteriocin that has been enzymatically or chemically truncated or cleaved. Such a fragment may encompass any portion of the native amino acid sequence of the bacteriocin.

The term "variant" refers to a natural or genetically engineered variation in amino acid sequence relative to the native bacteriocin amino acid sequence, such as one, two, three or more amino acid substitutions, deletions, or additions, natural allelic variants, or variations in post-translational processing.

The term "homolog" refers to a bacteriocin having an amino acid sequence homologous to the amino acid sequence of the bacteriocins discussed herein. Such homologous sequences are obtained from natural nucleic acid sequences (e.g., genomic DNA, cDNA), as well as synthetic or mutagenized sequences, by performing hybridization experiments under stringent conditions, wherein the nucleic acid sequences encoding homologs hybridize to DNA sequences encoding the amino acid sequences disclosed herein for a particular bacteriocin. For example, homologs to nisin are generally peptides whose nucleic acid sequence hybridizes to the nucleic acid sequence for nisin (SEQ ID NO:8) under stringent conditions. Such homologs would be expected to comprise an amino acid sequence that is approximately 90% to about 99.9%, preferably about 95% to about 99.9% homologous with that of the native amino acid sequence for nisin, and to exhibit similar structural and functional characteristics. Similarly, other bacteriocins will have homologs comprising amino acid sequences that are approximately 90% to about 99.9%, preferably about 95% to about 99.9% homologous with that of their respective native amino acid sequences. All such homologs would also be expected to form similar metal chelates and bind to target pathogens with the same characteristics of the bacteriocins described herein.

The term "stringent conditions" as used herein refers to hybridization performed using buffer containing relatively low salt and/or high temperature conditions, such as provided by 0.02M–0.15M NaCl at temperatures of 50° C. to 70° C. Such selective conditions tolerate little mismatch between the probe and the template or target strand, and would be particularly suitable for isolating homologous genes from related species or mutated genes.

The present invention thus also includes within its scope bacteriocin homologs encoded by DNA sequences capable of hybridizing, preferably under stringent conditions, with the DNA sequences described herein, or sequences which code for the bacteriocin amino acid sequences disclosed herein using the degeneracy of the genetic code and coding for proteins having substantially the same activity. Stringent hybridization conditions select for DNA sequences of greater than 85% or, more preferably, greater than about 90% homology. Screening of a cDNA library may be carried out under highly stringent conditions according to the method described in European Patent Application No. 88 119 602.9 and Kashima et al. (Nature 313:402–404 (1985)). The DNA sequences capable of hybridizing under stringent conditions with the DNA sequences disclosed in the present application may be, for example, allelic variants of the disclosed DNA sequences, may be naturally present in the particular microorganism but related to the disclosed DNA sequences, or may be derived from other sources. General techniques of nucleic acid hybridization are disclosed by Maniatis, T. et al., Molecular Cloning, a Laboratory Manual, Cold Spring Harbor, N.Y. (1982), and by Haymes, B. D. et al., Nucleic Acid Hybridization, a Practical Approach, IRL Press, Washington, DC (1985), and by Sambrook, J. and Russell, D. W., Molecular Cloning, A Laboratory Manual, 3rd Edition, Cold Spring Harbor, N.Y. (2001).

Amino acid residues in peptides are abbreviated as follows: Alanine is Ala or A; Cysteine is Cys or C; Aspartic Acid is Asp or D; Glutamic acid is Glu or E; Phenylalanine is Phe or F; Glycine is Gly or G; Histidine is His or H; Isoleucine is Ile or I; Lysine is Lys or K; Leucine is Leu or L; Methionine is Met or M; Asparagine is Asn or N; Proline is Pro or P; Glutamine is Gln or Q; Arginine is Arg or R; Serine is Ser or S; Threonine is Thr or T; Valine is Val or V; Tryptophan is Trp or W; and Tyrosine is Tyr or Y. Any of the amino acids may be replaced by a non-conventional amino acid. In general, conservative replacements are preferred, in which an original amino acid is replaced by a non-conventional amino acid that resembles the original in one or more of its characteristic properties (e.g., charge, hydrophobicity, steric bulk; for example, one may replace Val with Nval). The term "non-conventional amino acids" refers to amino acids other than conventional amino acids, and include, for example, isomers and modifications of the conventional amino acids, e.g., D-amino acids, non-protein amino acids, post-translationally modified amino acids, enzymatically modified amino acids, constructs or structures designed to mimic amino acids (e.g., α,α-disubstituted amino acids, N-alkyl amino acids, lactic acid, βalanine, naphthylalanine, 3-pyridylalanine, 4-hydroxyproline, O-phosphoserine, N-acetylserine, N-formylmethionine, 3-methylhistidine, 5-hydroxylysine, and nor-leucine), and other non-conventional amino acids, as described, for example, in U.S. Pat. No. 5,679,782 to Rosenberg et al. The peptides herein may also contain non-peptidic backbone linkages, wherein the naturally occurring amide —CONH— linkage is replaced at one or more sites within the peptide backbone with a non-conventional linkage such as an N-substituted amide, ester, thioamide, retropeptide (—NHCO—), retrothioamide (—NHCS—), sulfonamido (—SO$_2$NH—), and/or peptoid (N-substituted glycine) linkage. Accordingly, the peptides herein include pseudopeptides and peptidomimetics. The peptides of this invention can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides.

The term "Dhb" refers to didehydrobutyrine.

The term "Dha" refers to didehydroalanine.

The term "Dba" refers to diaminobutyric acid.

The term "bacterial pathogen" refers to any microorganism known to induce a disease in an animal, such as gram positive bacteria, gram negative bacteria, mycobacteria, and the like.

The term "non-bacterial pathogen" refers to fungi, viruses, prions, and the like without restriction. However, it is preferred that the bacteriocin metal complex binds to these pathogenic agents with an affinity constant of at least about $10^8$M.

The term "fusion protein" or "fusion construct" refers to a genetically engineered protein having an amino acid sequence comprising the amino acid sequence of one or more bacteriocins. The term "multimer" refers to a fusion protein comprising multiple copies of a bacteriocin amino acid sequence. The leader sequence may be included, however, the leader sequence is preferably deleted from the amino acid sequence of the fusion protein.

The term "sample" refers to any substance (e.g., food, water, beverage, pharmaceutical, cosmetic, waste product, synthetic product, etc.) or object (e.g., article of furniture or clothing, utensil, machinery, etc.) that it is desired to test for the presence of pathogens or non-pathogenic organisms.

The term "detectable" refers to detectable in any way, generally chemiluminescence.

The term "therapeutic treatment" refers to administration of the complexes to the epithelial surfaces in order to (1) prevent disease caused by a pathogenic organism, i.e., avoiding any clinical symptoms of the disease, (2) inhibit disease caused by a pathogenic organism, that is, arrest the development or progression of clinical symptoms, and/or (3) relieve the disease, i.e., cause regression of clinical symptoms.

The term "epithelial surfaces" refers to the outer layers of the skin, and includes mucosal epithelial surfaces such as the oral mucosa, intestines, vagina, or nasal mucosa.

"Patient" as used herein refers to any animal, preferably a mammal, and most preferably a human, who can benefit from the pharmaceutical formulations of the present invention.

The present invention provides novel bacteriocin-metal chelated complexes constituting a new class of chemiluminescent cell labels useful for rapid detection of gram positive pathogens and mycobacteria. The bacteriocin-metal chelates also may be used to detect non-bacterial pathogens. The invention further provides for a method of the manufacture of these labels and a method for use in a rapid detection assay for bacterial and non-bacterial pathogens.

A specific advantage of the present invention is the ability to detect viable cells. The bacteriocins bind to and form pores in functioning membranes. For example, the membrane-active channel-forming peptides of the Nisin family utilize the membrane potential of the living bacterium to bind and form a pore structure through the bacterial membrane. Thus, these bacteriocin-metal chelates serve as vital stains, and indicate the presence of viable bacteria.

It has been discovered that bacteriocins form a complex with redox-active metals requiring minimal chemical modification, and yield chemiluminescent bacteriocin-metal chelates. These bacteriocin-metal chelates appear to be as catalytically active as the oxidative enzymes and organometallic complexes of the porphyrins in catalyzing the hydrogen peroxide-mediated oxidation of luminol. Most significantly, these chelates are fully biologically active and are not sterically hindered by large enzymes or conjugated organic groups.

The present invention relates to the use of these bacteriocin-metal complexes as chemiluminescent probes for sensitive detection of bacterial and non-bacterial pathogens. A detection sensitivity for potential pathogens of 1 to 100 cells, preferably 5 to 20 cells, and most preferably 5 to 10 cells per sample. Contemporaneous assay of complex samples using immuno-magnetic capture of bacteria coupled with chemiluminescent detection can be performed. By coupling the immuno-magnetic capture technique with sensitive chemiluminescent detection, the analysis time is reduced from days to a few hours. In addition, the use of bacteriophage coupled with magnetic capture techniques is also advantageous.

In addition, these chemiluminescent probes can be used to study the biological affinity of bacteriocins to various organisms, particularly differing species of bacteria. While not being held to any particular theory, we hypothesize that there may be a correlation between bacteriocin affinity/binding and the resistance of a particular species to the bacteriocin. By correlating bacteriocin binding to pathogens using standard Minimal Inhibitory Concentration techniques to our titration data, a relationship between resistance and bacteriocin affinity may be demonstrated. The chemiluminescent bacteriocin binding assay can be used to examine the variables in bacteriocin resistance acquisition including, time course, environmental influences and effects of microbial flora.

The chelated complexes of the present invention are comprised of (a) a bacteriocin selected from the group consisting of lantibiotics, non-lanthionine containing peptides, large heat labile proteins and complex bacteriocins, fusion proteins thereof, mixtures thereof, and fragments, homologs and variants thereof, and (b) a detectable label comprising a transition or lanthanide metal.

II. Bacteriocins

Many organisms synthesize proteins or peptides which are degraded to smaller bioactive peptides having hydrophobic or amphipathic properties. For example, mammals synthesize defensins and cathelins, which provide antimicrobial activity in the intestines or leukocytes, for example. Various frog species synthesize magainins, dermnaseptins and bombinins, as well as other cationic peptides. Insects produce cecropins, defensins, apidaecins and diptericins, among others. The proteins and peptides in each family within this functional superfamily are homologous, but they exhibit little or no significant sequence similarity with members of the other families. Often, the peptides are cationic, which appears to play a role in their function of binding to and permeabilizing the membranes of invading microbes. These peptides generally exhibit antibiotic, fungicidal, virucidal, hemolytic or tumoricidal activities by interacting with membranes and forming transmembrane channels that allow leakage across cell membranes or bilayers.

Similarly, bacterial ribosomally synthesized antimicrobial polypeptides are generally referred to as bacteriocins. The bacteriocins fall into the following general categories:

Lantibiotics—post-translationally modified peptides, usually of less than about 5 kDa, which contain unusual amino acids such as lanthionine, beta-methyllanthionine and dehydrated residues. Modes of activity against target organisms range from membrane binding and pore formation, causing leakage of target cell membranes (class A), and specific inhibition of enzyme activity (class B). Class A lantibiotics include, but are not limited to nisin, lacticin 481, camocin U149, subtilin, epidermin, pep5, gallidermin, epilancin K7 and lactocin S. Amino acid sequences of these lantibiotics are shown in Table 1 below. Examples of class B lantibiotics include mersacidin, actagardine, cinnamycin and duramycin. The membrane binding and/or subsequent pore formation of class A lantibiotics, as well as the cationic defense peptides of non-bacterial origin, appears to be at least partially voltage dependent, and thus indicates the presence of viable cells.

Non-Lanthionine containing peptides—unmodified peptides, usually of about 10 kDa or less further categorized as follows: (i) listeria-active peptides, e.g., Pediocin PA-1, Sakacin A, Sakacin P, Leucocin A, Curvacin A, Mesentericin Y105, Carnobacteriocin BM1 and B2, Enterocin A, and Piscicolin 126; (ii) poration complexes consisting of two proteinaceous peptides, e.g., Lactacin F, Lactococcin G, Plantaricin E/F, Plantaricin J/K; (iii) thiol-activated peptides requiring reduced cysteine residues for activity, e.g., Lactococcin B.

Large Heat-Labile Proteins—larger proteins, generally having a molecular weight greater than 31 kDa, e.g., Helveticin V-1829.

Complex Bacteriocins—composed of a protein with one or more chemical moieties which may be of a lipid or carbohydrate nature, e.g., Pediocin SJ-1. For additional details, see Nissen-Meyer, J., et al., Arch. Microbiol. (1997) 167 (2/3): 67–77, and Sahl, H.-G., et al., (1998) Ann. Rev. Microbiol. 52:41–79.

The bacteriocins are bacterially produced peptide antibiotics with the ability to kill competing species bacteria, usually but not always those that are closely related to the producer bacterium. Many of the bacteriocins exhibit structural features typical of members of the eukaryotic channel-forming amphipathic peptides. They are usually synthesized as small precursor proteins or peptides that are processed by proteolytic elimination of the N-terminal leader sequences. The resulting mature peptides form one, two or more putative amphipathic transmembrane spanning portions. Where two membrane spanning portions are present, a characteristic hinge region that separates the two putative transmembrane segments is usually observed. A similar structural arrangement is observed in the Cecropin A proteins, having two transmembrane segments.

TABLE 1

CLASS A LANTIBIOTICS

| Name | Example | Amino Acid Sequence | |
|---|---|---|---|
| Gallidermin precursor | Gallidermin precursor of *Staphylococcus gaiinarum* | MEAVKEKNELFDLDVKVNAKESNDSGAE PRIASKFLCTPGCAKTGSFNSYCC | (SEQ ID NO:1) |
| Pep5 | Pep5 lantibiotic of *Staphylococcus epidermidis* | MKNNKNLFDLEIRKETSQNTDELEPQTA GPAIRASVKQCQKTLKATRLFTVSCKGKNGCK | (SEQ ID NO:2) |
| Mutacin BNY266 | Mutacin of *Streptococcus mutans* | FKSWSFCTPGCAKTGSFNSYCC | (SEQ ID NO:3) |
| Subtilin precursor | Subtilin of *Bacillus subtilis* | MSKFDDFDLDVVKVSKQDSKITPQWKSES LCTPGCVTGALQTCFLQTLTCNCKISK | (SEQ ID NO:4) |
| Nisin precursor | Nisin precursor of *Lactococcus lactis* | MSTKDFNLDLVSVSKKDSGASPRITSISLC TPGCKTGALMGCNMKTATCHCSIHVSK | (SEQ ID NO:5) |
| Epidermin precursor | Epidermin of *Staphylococcus epidermidis* | MEAVKEKNDLFNLDVKVNAKESNDSGAEP RIASKFICTPGCAKTGSFNSYCC | (SEQ ID NO:6) |
| Epilancin K7 precursor | Epilancin K7 of *Staphylococcus epidermidis* | MNNSLFDLNLNKGVETQKSDLSPQSASVL KTSIKVSKKYCKGVTLTCGCNITGGK | (SEQ ID NO:7) |

A. Lantibiotics

Lantibiotics are small membrane-active channel-forming peptides having a molecular weight less than about 5 kDa. The lantibiotics form a useful group of bacteriocin-metal complexes suitable as catalytically active chemiluminescent agents, and include nisin and related peptide antibiotics, illustrated in FIG. 1. The nisin family belongs to a family of defense peptides containing the unusual post-translational thioether modification, lanthionine and beta methyl-lanthionine, called lantibiotics. Lanthionine is a residue formed by post-translational processing, which is two alanine residues bonded to sulfur at the beta carbonyls (13). The peptides are produced by cytoplasmic dehydration of the hydroxy-amino acids followed by Michael addition of the SH groups of cysteine residues in the peptide to the vinyl groups formed. The thioether amino acids formed by these concerted reactions are termed lanthionine or beta-methyl-lanthionine.

Figure 2:
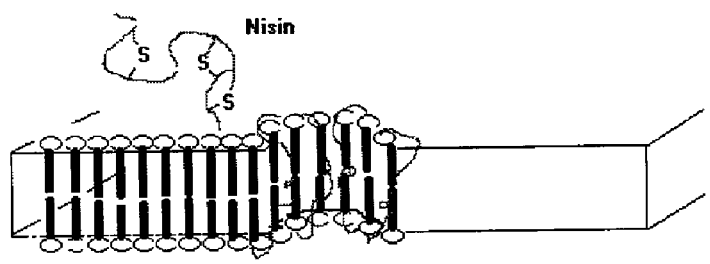
FIG. 2 schematically illustrates a model of the self-assembled aggregate pores in the cytoplasmic membranes of susceptible bacteria formed by the lantibiotics.

Certain of the lantibiotics and other bacteriocins work by forming self-assembling aggregate pores in the cytoplasmic membranes of susceptible bacteria. Binding of the bacteriocin to the membrane leads to aggregation and oligomerization of bacteriocins, which then adopt a transmembrane orientation so that the hydrophobic portion is exposed to the core of the membrane and the hydrophilic part forms the aqueous channel, as shown in FIG. 2. The pores impose a loss of vital salts, cofactors and other materials necessary for cellular respiration and metabolism. The remarkable utility of these agents as diagnostics resides in their functional activity only toward viable bacteria. Cells which lose their transmembrane electrical potential do not support the self-assembly function of the antibiotic, as both membrane insertion and pore formation require a transmembrane potential.

While wishing not to be bound by theory, it is hypothesized that the thioether groups of the unusual amino acids and the amino groups provided by lysine residues of the lantibiotics provide ligands for chelating transition and lanthanide metals. The lantibiotics also form cyclic structures, which allows for the creation of many hairpin turns in these peptides, and is associated with binding transition metals and lanthanide metals.

While lantibiotics are the preferred bacteriocins, any of the generally cationic peptides synthesized by bacteria, plants, mammals or insects having antimicrobial activity and forming complexes with transition or lanthanide metals could be used. Therefore, diverse species of cationic membrane active peptides such as the non-lanthionine containing bacteriocins, defensins, cecropins, and magainins, for example, are equally useful to generate metal complexes which bind to the membranes of pathogens, and can be used for the detection of pathogenic species. Fusion proteins, fragments, homologs and variants of these cationic peptides also are encompassed within the present invention, so long as membrane binding activity is preserved. However, the function of pore formation is not necessary for detection, and therefore, the bacteriocins or other cationic antimicrobial peptides, fusion proteins thereof, fragments, homologs and variants thereof are included even if the pore forming activity has been lost due to changes in amino acid sequence or secondary structure. Preferably, the present invention is applicable to any bacteriocin capable of binding to gram positive bacteria, mycobacteria, gram negative bacteria, and fungi. Gram positive bacteria are preferred targets for the bacteriocin-metal complexes of the present invention. In certain embodiments, permeabilized gram negative bacteria and fungi may be targeted.

*Lactobacillus lactis* subspecies can produce diplococcin, lactococcin, lactostrepcins or nisin. Diplococcin and lactococcins are small molecular weight proteins, active against other *lactococci* while nisin is a lantibiotic with a broad spectrum of activity against many Gram positive bacteria.

Nisin is the most extensively characterized bacteriocin of the antimicrobial proteins produced by lactic acid bacteria and has found widespread application in the food industry. Nisin was the first "lantibiotic" compound to be used on a commercial scale in the food industry. It is used to prevent spore outgrowth and toxin production by *Clostridium botulinum* in processed cheese and cheese spreads. In some countries, it has been used to extend the shelf-life of dairy products and to prevent the spoilage of canned foods by thermophiles.

Nisin is a pentacyclic, class A lantibiotic and displays an amphiphathic character, with a hydrophobic residue (Ile) at its N-terminus and a hydrophilic residue (Lys) at its C-terminus. It is a peptide of 34 amino acids and contains one lanthionine residue, four beta-methyllanthionines, a dehydroalanine and a dehydrobutyrine. The thioether amino acids, (lanthionine and beta-methyllanthionine) account for the high sulphur content of nisin. The usual amino acid residues are thought to be responsible for the important functional properties of nisin, e.g., the associated acid tolerance and thermostable properties of nisin are attributed to the stable thioether linkages while the specific bactericidal activity is thought to be due to the very reactive double bonds. Nisin has a molecular mass of 3.5 kDa and often forms dimers and oligomers.

As reviewed by Sahl et al., (*Ann. Rev. Microbiol.* (1998) Vol. 52, pages 41–79), the lantibiotics comprise several classes of compounds, as indicated by various mechanisms of action. For example, nisin and related peptides (type A) appear to be bacteriocidal by virtue of their pore forming ability, while type B lantibiotics appear to exert their activity through interfering with enzyme activity by blocking the respective substrate. For example, Mersacidin, a type B lantibiotic, binds to lipid II.

An especially preferred lantibiotic for use in a bacteriocin-metal complex is nisin. We have discovered that nisin chelates transition metals such cobalt and iron without compromising its cellular binding function. Cobalt chelates of nisin can be easily prepared by dissolving nisin in aqueous solution and treating the solution with a cobalt salt to form the chelate. Furthermore these chelates are also active in the hydrogen peroxide-driven oxidation of luminol.

Exemplary members of the nisin family include nisin, mutacin, subtilin, gallidermin, Pep5, epicidin 280, epilancin K7, lactocin S, streptococcin A-FF22, lacticin 481, salivaricin A, variacin, cypemycin, mersacidin, cinnamycin, duramycin and ancovenin, actagardine, sublancin, plantaricin C, fusion proteins thereof, mixtures thereof and fragments, homologs and variants thereof. It is intended that all similar lantibiotic structures also be encompassed within this invention. For example, a truncated form of one of the above listed lantibiotics may function adequately to bind to viable bacteria, and may likewise form the antibiotic-metal chelate and act as a chemiluminescent probe of the present invention. Similarly, a mutant having a slightly different amino acid sequence may also function adequately, and thus is included within the invention as described herein.

A wide variety of nisin and related lantibiotic mutants and variants have been studied. Studies have shown that the Dhb residues in the central portion of Pep5 appear to stabilize the three-dimensional conformation of this peptide. If Ala is substituted for Dhb, the antibacterial activity is lost. Subtilin may be made more stable by substituting Glu4 for Ile. Similarly, nisin has been engineered to be more stable, (Dha5Dhb nisinZ), or more soluble (N27K nisin Z, H31K nisin Z). Gallidermin may be made more stable to trypsin (Dhb14Por A21L) and Pep5 may be made more stable to chymotrypsin (A19C Pep5). T2S nisin Z, L6V gallidermin and M17Q/G18T nisin Z show an enhanced antibacterial activity with at least some strains. Therefore, it is clear that variations in the amino acid sequences and post-translational processing of nisin and related peptides are possible. All such variations resulting in active metal chelates that bind to target bacteria or other pathogens are considered to be encompassed within the present application.

Nucleotide sequences for the above lantibiotics are also well known in the art. For example, the nucleotide sequence which encodes the amino acid sequence for nisin from *Streptococcus lactis* is as follows:

```
                                                              (SEQ ID NO:8)
  1 agttgacgaa tatttaataa ttttattaat atcttgattt tctagttcct gaataatata 61 gagataggtt tattgagtct tagacatact tgaatgacct agtcttataa ctatactgac 121 aatagaaaca ttaacaaatc taaaacagtc ttaattctat cttgagaaag tattggtaat 181 aatattattg tcgataacgc gagcataata aacggctctg attaaattct gaagtttgtt 241 agatacaatg atttcgttcg aaggaactac aaaataaatt ataaggaggc actcaaaatg 301 agtacaaaag attttaactt ggatttggta tctgtttcga agaaagattc agtgcatca 361 ccacgcatta caagtatttc gctatgtaca cccggttgta aaacaggagc tctgatgggt 421 tgtaacatga aaacagcaac ttgtcattgt agtattcacg taagcaaata accaaatcaa 481 aggatagtat tttgttagtt cagacatgga tactatccta tttttataag ttatttaggg 541 ttgctaaata gcttataaaa ataaagagag gaaaaaacat gataaaaagt tcatttaaaq 601 ctcaaccgtt tttagtaaga aatacaattt tatctccaaa cgataaacgg agttttactg 661 aatatactca agtcattgag actgtaagta aaaataaagt tttttggaa cagttactac 721 tagctaatcc taaactctat gatgttatgc agaaatataa tgctggt
```

Therefore, also included within the present bacteriocin-metal complexes are amino acid sequences encoded by SEQ ID NO:8 as well as nucleic acid sequences which hybridize with SEQ ID NO:8 under stringent conditions. Amino acid sequences comprising the amino acid sequence of SEQ ID NOS:1–7, having substitutions, insertions, deletions and additions of one, two, three or more amino acids would also be within the scope of the present invention.

Enzymatically or chemically derived fragments of these bacteriocins are also encompassed by the invention. Mutations, truncations, homologs and natural variants likewise are included within the scope of the invention. Engineered variants such as fusion proteins or constructs comprising the amino acid sequence of one or more bacteriocins may also be utilized in the present invention. A particularly preferred embodiment is a fusion protein comprising multiple copies of a bacteriocin. A preferred bacteriocin for constructing a multimer of bacteriocins is nisin. In some instances, the fusion construct is a multimer of one particular bacteriocin. In other instances, the fusion construct is a multimer of different bacteriocins. Spacer sequences comprising an amino acid sequence of between about 5 to about 25 amino acids, preferably between about 1 to about 10 amino acids, may be included between the C-terminus of one subunit of bacteriocin and the N-terminus of the next bacteriocin. Any of the above variations in bacteriocin structures may be used as probes providing that the bacteriocin variant forms a chelated complex with the metal, and the bacteriocin-metal complex binds to pathogen, particularly gram positive bacteria and mycobacteria. In some instances, the pathogen is a gram negative bacterium, or fungi. Non-pathogenic organisms may also be targeted and detected if this is desired, provided that the bacteriocin binds to the non-pathogenic target organism.

Fusion proteins comprising the amino acid sequences shown above as well as those encoded by nucleic acid sequences comprising SEQ ID NO:8 are also included in the present bacteriocin-metal complexes, as are multimers comprised of one or more repeats of the nisin amino acid sequence shown above (SEQ ID NO:5), preferably with the leader sequence removed. An advantage of fusion constructs comprising bacteriocin sequences is that additional metals will be present in the complex, and higher catalytic efficiencies can be achieved, resulting in even greater sensitivity of detection.

Non-lantibiotic bacteriocins, such as plantaricin, thermophilin and mesentericin Y are also useful bacteriocins and may be used to generate metal complexes and used to detect pathogens or other analytes. Any of the ribosomally synthesized cationic defense proteins that bind to the cytoplasmic membranes of target bacteria or other pathogens are included within the present claims.

III. Target Pathogenic Species

The complexes of the present invention preferentially bind to gram positive cells. In certain preferred embodiments of the invention, the complexes are capable of binding to mycobacterial cells. In particular embodiments, the bacterial cells are pneumococci, streptococci, staphylococci, aerobic bacilli, lactobacilli, enterococci, anaerobic clostridia, leuconostocs, micrococci, pediococci, actinomyces, listeria and nocardia. In other embodiments, the bacterial cells are mycobacterium *tuberculosis*, mycobacterium *avium*, mycobacterium *paratuberculosis*, mycobacterium *bovis* and mycobacterium *leprae*.

The complexes of the present invention are also capable of binding to and detecting permeabilized gram negative bacterial cells. The outer membrane of gram negative bacteria excludes substances such as bacteriocins, thus preventing the bacteriocin from making contact with the cytoplasmic membrane. The gram negative bacterial cells may be permeabilized by treating the cells with a chelating agent (e.g., EDTA) such that the structure of the outer membrane undergoes alteration, resulting in destabilization of the lipopolysaccharide (LPS) layer with a corresponding increase in cell permeability. Another method of permeabilizing gram negative cells is by pre-treating the cells with the non-toxic fragment of polymyxin B, polymyxin B nonapeptide, which renders gram-negative bacteria susceptible to substances known to be unable to pass through the outer membrane envelope. These permeabilization methods do not kill the bacteria and so are a useful method of rendering the gram negative bacterial cell membrane susceptible to detection using the bacteriocin-metal complexes described herein.

Permeabilized gram negative bacteria that may be targeted by the present bacteriocin metal chelates include, but are not limited to, *neisseria, Flavobacter* and *salmonella*, as well as *Enterobacteriace* and all other classes of aerobic and anaerobic gram negative microorganisms, that have been permeabilized such that the bacteriocin-metal complexes of the present invention are permitted access to the cell membrane.

When the bacteriocin-metal complex comprises nisin, a very broad spectrum of activity against gram-positive vegetative bacterial cells is observed. The closely related lactococci are especially preferred but nisin-metal complexes are also active against several strains of bacilli and clostridia, lactobacilli, leuconostocs, micrococci, pediococci, streptococci and actinomycetes. Other detectable strains include *Mycobacterium tuberculosis, Staphylococcus pyogenes, S. aureus, S. epidermidis* and *Listeria monocytogenes* (de Vuyst & Vandamme, 1994). Certain gram negative strains such as *Neisseria* (Mattick & Hirsch, 1947) and *Flavobacter* (Ogden & Tubb, 1985) may also be targeted. *Salmonella* subspecies and other gram negative bacteria can be detected using bacteriocin-metal complexes comprising nisin provided that the bacteria are permeabilized.

Under normal circumstances, nisin does not inhibit yeasts or viruses. However, the bacteriocin-metal complexes are capable of binding to fungal membranes in the presence of an agent that inhibits the biogenesis of a normal fungal cell wall, or in the presence of a cell wall lytic enzyme. Thus, the bacteriocin-metal complexes are also active against fungal membranes, and may be used to target fungal infection or contamination. In particular, the bacteriocin-metal complexes may by used in the detection and diagnosis of fungal diseases, for example cryptocossis, histoplasmosis, blastomycosis, coccidioidomysis, sporotrichosis, chromoblastomycosis, aspergillosis, zygomycosis, and candidiasis. Candidiasis is a preferred target for detection and diagnosis. Inhibition of the biogenesis of a normal fungal cell wall can be effected, for example by providing agents that inhibit the anchorage of cell wall proteins into the cell wall of the fungi, beta-(1,6)-glucose polysaccharides or branched polysaccharides having a beta-(1,6)-glucose-backbone, such as beta-gentiobiose and pustulan fragments, and mixtures thereof.

Alternatively, fungi may also be targeted by the bacteriocin-metal chelate when the fungi have been treated with a cell wall lytic enzyme, such as chitinase or a glucanase, or, more preferably, a mixture of them. The preferred glucanase is beta-1,3-glucanase, optionally admixed with beta-1,6-glucanase. The enzyme(s) can be used as a separate, more or less pure enzyme isolate, but combinations of the enzymes are preferred. Crude preparations from natural origin containing the enzymes are commercially available and can be used instead of purified enzymes. One such enzyme preparation is marketed as NovoZyme™ 234, ex NOVO, Denmark, which is a mixture of lytic enzymes containing, inter alia, chitinase as well as beta-1,3-glucanase and small amounts of beta-1,6-glucanase. Such a preparation is produced by fermentation of the fungus *Trichoderma harzianum* according to U.S. Pat. No. 4,353,891, and described in WO 90/03732. Other natural mixtures of chitinase and said glucanases can be obtained from vegetable sources, particularly from plants which are able to produce glucanase and chitinase as described in e.g. Plant Physiology 101: pp 857–863. Chitinase as well as glucanase are preferably used in a concentration of 0.001–2 wt. % calculated on the composition. The amount of bacteriocin, preferably nisin, is 0.00001–0.1 wt. %, preferably 0.0001–0.02 wt. % calculated on the composition. The preferred ratio of chitinase and beta-1,3-glucanase is 1:9 to 9:1. Concentrations and ratios may be easily optimized depending on the actual composition ingredients.

IV. Metals of the Bacteriocin-Metal Complex

Co-pending U.S. patent application Ser. No. 09/687,990, filed Oct. 13, 2000, discloses that antibiotics of the polymyxin and colistin type tightly bind a range of metals in aqueous solution. It has been further discovered that bacteriocins will spontaneously chelate metals in aqueous solution, and that these bacteriocin-metal complexes bind to viable cells, but not to dead cells.

The preferred metals of the present invention include the transition metals and the lanthanides. The transition metals are particularly preferred because of their high oxidation-reduction activity in neutral aqueous media. It is likely that these metals catalyze the process of oxidizing chemiluminescent substrates, such as luminol by hydrogen peroxide (Rost et al. (1998) *J. Biolumin. Chemilumin.* 13:355–363). The bacteriocin-metal complexes can directly catalyze peroxide-driven chemiluminescent reactions (for example, reactions involving luminol, its aromatic derivatives, lucigenin, penicillin, luciferin and other polyaromatic phthalylhydrazides) without the use of an enzyme catalyst such as horseradish peroxidase or microperoxidase.

Factors influencing the catalytic efficiency of individual metals include pH, ionic strength and oxidation state. Chelation chemistries that would alter the oxidation state or steric availability of the metals during catalysis could also influence the optimum catalytic activity as sensed by the time dependent emission of photons. The transition metals, cobalt, copper and chromium are preferred metal complexes because of their inherently high catalytic efficiency for the peroxide-driven oxidation of luminol (10). There may be other redox-active metals which could be as efficient or more than the aforementioned metals.

Preferably, although not necessarily, the metal in the complex is a transition metal or a lanthanide metal; more preferably it is copper, cobalt, iron, manganese, chromium, nickel, zinc, terbium, gadolinium, europium, or technicium. The metal is generally provided as an aqueous soluble salt and at an oxidation state of +2 or +1.

Preferred transition metals measured in the bacteriocin-metal complex of the present include iron (Fe), copper (Cu), cobalt (Co), chromium (Cr), nickel (Ni), manganese (Mn), zinc (Zn) and technicium (Tc). The most preferred metals, iron, cobalt, manganese and chromium, yield the most catalytically active complexes on a molar basis. Cobalt and chromium complexes are especially preferred.

Another preferred class of metal chelates of the present invention comprise heavy metals in the lanthanide series, gadolinium (Gd), lanthanum (La), europium (Eu), terbium (Tb), dysprosium (Dy), lutetium (Lu) and erbium (Er).

A unique and useful aspect of terbium and europium complexes is that neither the metal salts nor the antibiotic are fluorescent; however, some of the chelates are fluorescent. For example, upon addition of the lanthanide salts, terbium or europium chloride, to solutions of polymyxin, a blue fluorescent emission can be observed at 400–450 nm when illuminated with 330 nm light. The polymyxin B-terbium complex is also useful as an epifluorescence microscopy label for *E. coli* and *Salmonella* cells. Similarly, these lanthanide metals form fluorescent complexes with the bacteriocins, preferably nisin.

Many of these bacteriocin-metal complexes have optical properties, e.g. fluorescence, UV or visible light absorption. For example, polymyxin B-metal complexes of terbium and europium are fluorescent and provide a visible emission in the blue band when excited with 350 nm light; polymyxin B-metal complexes of iron and cobalt are colored and can readily be followed by spectrophotometry using techniques known to those of ordinary skill in the art and described in the pertinent texts and literature. Thus, the polymyxin-metal complex can be readily purified using standard chromatographic techniques such as gel filtration or dialysis procedures because it can be followed visually with either visible absorbance or fluorescence depending on the type of complex. Similarly, the bacteriocin metal chelates of the present invention are readily formed and purified.

The binding interaction between the bacteriocin and metal is sufficiently tight to permit isolation of the bacteriocin complex by gel filtration or dialysis, which would ordinarily separate high molecular weight compounds from simple metal salts. The strong absorbance bands exhibited by the bacteriocin-metal complex permit the absorbance of the peptide chromophore at 270 nm and the visible absorbance bands at 400 nm to be used to follow purification of the complex. The efficient chelation of metals is presumably due to formation of a cleft within the structure of the bacteriocin, providing both carbonyl oxygens and amide nitrogens to contribute electron density for orbital overlap in the outer electron orbitals of a metal atom. While not wishing to be bound to any particular theory, it is hypothesized that many species of bacteriocins are capable of forming the chelated complex of the present invention, and being capable of binding to viable microbial cells. Hairpin structures in peptides also lend themselves to forming metal complexes. The lantibiotics may also form complexes with metals via the thioether moieties that can act as ligands for metals. Certain of the bacteriocins, the lantibiotics in particular, are strongly cationic and may form complexes via their amino groups.

The bacteriocin-metal chelate is preferably a chelated metal complex containing one metal atom. The metal may be coordinated at four, five or six sites. Preferably, the metal binding site is within the cleft formed by the cyclized amino acids or other three dimensional structure formed by the bacteriocin. A preferred bacteriocin is one that forms a molecular cleft and retains bacterial binding activity, particularly with respect to viable bacteria.

Optionally, addition of metal chelating ligands is possible with these bacteriocins. Reductive alkylation with aromatic carboxaldehydes, the monocarboxaldehyde of 2,2'-dipyridine, salicylaldehyde or protocatechualdehyde, for example, would add a suitable metal binding cavity to the bacteriocin molecule to chelate several transition metals such as copper, nickel, zinc, technetium, and preferably cobalt, iron, manganese, or chromium. The aforementioned ligands, including 2,2-dipyridyl monocarboxlic acid, salicylic acid, and protocatechuic acid, could alternatively be grafted onto the bacteriocin through an amide linkage as preformed, isolated N-hydroxysuccinimide esters. The ligands could either be used pre-loaded with the metals as reactive chelates, or optionally, chelated after the conjugates are formed.

V. Pathogen Capture

Pathogens present on or in the sample may be removed from the sample to be tested by washing or other physical methods for sample preparation. For example, the sample may be contacted using a swab and any organisms present on the swab can be suspended into aqueous buffer solution. The pathogens on the surface or within the sample may also be washed off using buffer, disrupting the structure of the sample if necessary, by mincing or shredding the sample, for example. Alternatively, the pathogens may be disassociated from the sample by sonicating the sample in buffer. Buffer solutions containing high salt, low or high pH, or additional solvents may also be used to disassociate the pathogens from the sample to be tested.

In a preferred method, the sample may be treated first with the bacteriocin and metal such that any pathogens present become labeled with the bacteriocin-metal complex. Such in situ labeling can be performed prior to the removal of pathogens from the sample. Alternatively, once the pathogens are removed from the sample, the pathogens may be labeled with the bacteriocin-metal complex.

The pathogens isolated from the sample may be concentrated by centrifugation, filtration or drying. Alternatively, adsorptive particles (e.g. magnetic immuno-microbeads or phage-microbeads) may be used to concentrate the sample containing pathogens. Microbeads are beads consisting of polystyrene or other synthetic latex, polymer coated ferrite or super-paramagnetic materials, silica micro-beads or cross-linked polysaccharide micro-beads, for example. Preferred microbeads are non-porous monodisperse superparamagnetic particles comprising polystyrene and divinyl benzene with a magnetite core $(8\pm2\times10^{-3}$ cgs units) and a diameter of about 2–5 µm. Microbeads with reactive groups on their surfaces (e.g., SH, OH, $NH_2$, COOH, tosyl, etc.) are commercially available. These microbeads can be used for covalent attachment of proteins or nucleic acid ligands, but there is no limit to substances that can be attached to the microbeads. For example, beads which have streptavidin attached can be used to bind a component from a sample that is attached to biotin.

Similarly, antibodies or antibody fragments (e.g., Fab) specific for one or more target pathogens can be attached to magnetic microbeads via the reactive groups in order to facilitate isolation and concentration of the pathogen for quantitative or qualitative testing. The target pathogen can be isolated using specific antibodies attached to microbeads and the bacteriocin-metal complex is allowed to bind to the pathogen either before or after isolation of the pathogen. For example, rapid capture of *Listeria* cells in a complex sample can be effected using anti-*Listeria* antibody on magnetic microbeads. Use of this immuno-microbead method requires obtaining or preparing antibodies specific for *Listeria* and attaching them to the reactive groups on the microbeads. Antibodies with a broader range of specificities to target pathogens (e.g., antibodies that bind to peptidoglycan or lipopolysaccharide) can also be attached to microbeads, and bacteriocin-metal complexes of more or less desired specificity can be used as a probe for particular species.

A preferred method of isolating target bacterial pathogens is using microbeads having attached bacteriophage, phage ghosts or purified phage sheath proteins. The selective binding function of the phage or purified phage sheath proteins is preferable to using antibodies because phage for particular target species are readily available and can be very specific. A bactreriophage specific for *Listeria* could be attached to microbeads. For example, B1 Phage of *Listeria monocytogenes* (ATCC 23074), is commercially available, and when attached to microbeads, can be used as a *Listeria* specific reagent. One could also inactivate purified phage particles using hypo-osmotic shock, rapidly dilution into distilled water, or by brief exposure to low pH, causing the loss of phage DNA. The phage "ghosts" are then immobilized on activated magnetic particles (e.g. tosyl-activated particles) in much the same manner as antibodies are immobilized.

In another embodiment, the phage sheath protein carrying the recognition site for *Listeria* cell walls is purified from intact phage particles and attached to microbeads. The Phage sheath protein can also be genetically engineered as a fusion peptide comprising a nickel-binding site to permit affinity purification from crude *E. coli* lysates once cloned into the appropriate expression vector. A similar approach preparing fusion proteins containing the endolysin protein is described in Loessner, M. et al. *Modified Listeria Bacteriophage Lysin Genes (ply) Allow Efficient Overexpression and One-Step Purification of Biochemically Active Fusion Proteins*. Appl. and Environm. Microbiol. 62, 3057–3060 (1996). Using either purified phage sheath protein, phage ghosts, or fusion proteins comprising the sequence for phage sheath protein, the phage is then attached to microbeads and used as a *Listeria* specific capture agent. The bacterial pathogen, in this example *Listeria*, can be treated with the bacteriocin-metal complex either before isolation or after isolation from the sample being tested. Detection and quantitation is effected in both cases by the chemiluminescence of the bacteriocin-metal complex in the presence of an oxidizable substrate and a source of peroxide.

Similarly, bacteriophages specific for other organisms can be used as pathogen specific reagents for isolating the pathogens for ease of quantitative and qualitative analysis. For example, *Staphylococcus aureus* (subsp. *aureus* Rosenbach) is specifically targeted using bacteriophage P1 (ATCC 11987). The range of bacteriophages available and the bacteria for which they are specific will be realized to be vast by those skilled in the art. For example a list of phage types is available from the American Type Culture Collection (ATCC). Other such depositories also publish equivalent data in their catalogues and this may be used to identify possible phage "reagents" for the present method. Phages may be used, inter alia, in aqueous suspension or in freeze dried form e.g. on microtiter plate wells. In this manner plate luminometry can be used.

In addition to phages deposited with a depository, an additional source of phages is provided by isolating them from suitable environments, such as the environment where the target bacteria are themselves to be found. For example, it is possible to isolate phages specific to both *Campylobacter* spp. and *Salmonella* spp. from effluent from a poultry processing plant. Isolation techniques will be well known to those skilled in the art and are exemplified, for example, by Loessner and Busse (1990) Appl. and Environm. Microbiol. Vol 56, pp 1912–1918, and Adams "Bacteriophages" Pub Interscience Inc (1959) pp 447–455. Isolation of additional bacteriophages that can be used in the present methods is described in U.S. Pat. No. 6,322,783.

The range of media available for selective promotion of growth of a particular bacterial type will also be known to those skilled in the art and these may function by positive action or by e.g. inhibition of other organisms. Examples of such media are illustrated by reference to supplier's manuals, e.g. such as those available from UNIPATH Limited, Wade Road, basingstoke, HANTS, RG24 OPW, UK "Selective Microbiology for Food and Dairy Laboratories", or e.g. the OXOID manual. These publications list, for example, media capable of favoring growth of *Campylobacter, Listeria* and *Yersinia*. Similarly methods for isolation of food pathogens for preparation of test samples are well known. (UNIPATH and OXOID are Registered Trade Marks). Additional useful references are the microbiology manuals: Bergey's Manual of Systematic Bacterial Classification and the DIFCO manual.

Numerous methods are known in the art for covalently attaching chemical moieties to surfaces, for example magnetic particles. Any of the art-recognized methods can be used, for example, cross-linking reagents, chemical derivatization methods, etc. to attach intact phage, phage ghosts or phage proteins to microbeads or other capture agent. Alternatively, antibodies or antibody fragments specific for the phage can be attached to the surface of the microbead, and used to bind pathogens from a sample, when phage has been added to the sample to bind the pathogen with high binding specificity. As will be appreciated, other variations are also possible, and are encompassed within the disclosed method of utilizing phage for specific capture of pathogens.

In some instances, it may be desirable to test a biological sample in a more invasive manner to test for intracellular pathogens or adherent pathogens. Intracellular pathogens include such organisms as parasites (e.g., *Rickettsia, Chlamydia, Plasmodia*), viruses (e.g., viral genes or expression products), or aberrant proteins associated with a pathological condition (e.g., prions). Adherent pathogens are pathogens that bind strongly to host tissue, for example, using pili, and may not be removed by washing. Such biological samples may be treated to generate a cellular suspension, such as by homogenizing the tissue, or may even be disrupted so that cellular contents are released. Intracellular pathogens or pathogens present in cell suspensions may be captured and detected using antibody or phage attached to microbeads. Alternatively, these pathogens may be detected using a chemiluminescent agglutination assay, as described in detail below.

Finally, once pathogens have been removed from the sample by phage or antibody binding, the number of organisms present is determined by measuring the luminescence in the presence of an oxidizable substrate (e.g., luminol) and a source of peroxide. Preferred separation methods for target pathogens include immuno-sedimentation using either magnetically accumulated micro-beads or gravity sedimentation. Filtration of bacteria or fungi from buffer solution can also be performed. Several methods for isolation of pathogens from food and water have been published, e.g., Fratamico (1992) *Food Microbiol.* 9:105–113, and Pyle (1999) *Appl. Environm. Microbiol.* 65:1966–1972). Use of these immuno-sedimentation techniques provide several advantages over the aforementioned alternative selective methods such as speed, simplicity, minimization of handling, and elimination of the need for incubation equipment.

VI. Methods of Bacteriocin-Metal Complex Preparation

Bacteriocin-metal complexes are readily prepared in aqueous solution (e.g., an aqueous buffer), although non-aqueous solvents and/or mixed solvents can be used provided the metal salt and bacteriocin are sufficiently soluble to form a chelated complex and bind to pathogens present in or on the sample. If using a buffer, volatile buffers, such as acetic acid, ammonium acetate, and ammonium bicarbonate are preferred. Crystalline or powdered bacteriocin is dissolved to form a concentrated solution, preferably greater than 0.5 M, and water soluble metal salts are added to provide a slight molar excess over the bacteriocin. Chelates formed in solution can be isolated by separating the free metal from the bacteriocin. A preferred method of desalting the complex is dialysis or gel filtration (e.g., dialysis in narrow-pore molecular weight cut-off tubing for example, from Spectro-Por, or by gel filtration on GPC media such as Sephadex G-25). The purified bacteriocin-metal complex can be dried if desired, preferably by freeze drying or, alternatively, by spray drying. Preferred methods for the preparation of particular bacteriocin-metal complexes can be readily ascertained by those skilled in the art.

Bacteriocin-metal complexes isolated by the aforementioned procedures can, optionally, be further characterized by combustion analysis, NMR, and electronic spectroscopy, for example. These procedures should also be accompanied by a bio-assay method to ensure preservation of bacterial binding activity, and/or anti-microbial activity. A bio-assay can be conducted as follows: Bacteria, diluted to a cell concentrations of 1–100 CFU/mL, preferably 10 CFU/mL, are treated with a bacteriocin-metal complex (e.g., nisin-Co (II) complex (as described in example 1) at 0.1 to 1000 µg/mL, preferably 1 to 100 µg/mL, and most preferably 30 µg/mL, at room temperature for a time sufficient to achieve binding (usually 5 to 60 minutes). The cells are removed, by for example, centrifugation, magnetic microbeads, or other method of pathogen capture, washed and resuspended in assay solution. Chemiluminescence is measured after the addition of oxidizable substrate and peroxide, (e.g., Luminol reagent purchased from NEN Life Sciences (Boston, Mass.) and using a Luminator® luminometer). The minimum number of cells that are detectable using the chemiluminescent bacteriocin-metal complexes is approximately 10 to 100 cells per sample. When a multimer of bacteriocins is utilized to form the bacteriocin-metal complex, the bio-assay has even greater sensitivity.

Alternatively, an end-point determination for Minimum Inhibitory Concentration (MIC) of the bacteriocin can be conducted according to standard microbiological procedures. MIC is determined by testing the ability of bacteria to grow in the presence of varying concentrations of an agent to be tested for anti-microbial activity. One variation of this procedure is performed as follows. Other variations of this general protocol are of course within the ability of one skilled in the art. A stock culture of ~$10^8$ CFU/ml is used to inoculate a 5 ml portion of Trypticase Soy Broth, using a 0.1 ml aliquot. An anti-microbial agent is added to the inoculated samples, at concentrations ranging from about 1 µg/ml to about 100 µg/ml, and the samples are grown for 24 hours in a 37° C. incubator. The sample turbidities are compared with negative controls containing no anti-microbial agent. The minimum concentration yielding no bacterial growth is the MIC.

VII. Utility

A. Diagnostic and Analytical Assays

The bacteriocin-metal complexes can be used to detect the presence of any analyte, provided antibodies with specificity for the analyte are available. A general method for conducting a chemiluminescent agglutination assay is as follows: (a) providing *Staphylococcus aureus* cells with antibodies to an analyte bound thereto, (b) contacting a sample with the *Staphylococcus* cells, (c) allowing the antibodies to bind to the analyte and agglutinate the *Staphylococcus* cells, (d) separating the agglutinated cells from the non-agglutinated cells, (e) contacting the agglutinated cells with a bacteriocin and a transition or lanthanide metal, (f) removing unbound complex and (g) detecting the presence of the analyte by contacting the sample with a peroxide source and an oxidizable substrate.

For example, intracellular pathogens or other analytes can be detected using an agglutination assay utilizing antibodies specific for these pathogens or analytes and *Staphylococcus aureus* cells. The *S. aureus* cells bind the Fc portion of the antibody and, in the presence of the antigen, in this case, the intracellular pathogen, become aggregated. Agglutinated cells can be separated from non-aggregated cells using filtration on narrow pore size membrane filters, which allow non-aggregated cells to pass, while retaining aggregated cells. The cells are then detected in situ on the filter by adding the bacteriocin-metal complexes described herein. If desired, any unbound complex can be removed, for example, by washing. The bacteriocin-metal complex, now bound to the agglutinated *S. aureus* cells, can be detected using chemiluminescence. By this procedure, pathogens other than gram-positive and gram-negative bacteria and fungi can be tested and detected. This procedure is most preferred for testing and detecting viruses and prions or prion-like proteins. Food samples or food preparation surfaces can conveniently be tested for the presence of these difficult to detect pathogens. In the veterinary context, it would be very useful to screen and detect diseases in animals (e.g., scrapie, Bovine Spongiform Encephalopathy, hoof and mouth disease). The agglutination assay can of course be used for any pathogen species, and is not limited to intracellular pathogens. The agglutination assay is also very sensitive, since in principle, as few as five pairs of agglutinated cells can be detected.

In an assay for bacterial pathogens, the presence of pathogenic cells can be detected using bacteriocin-metal complexes and measuring chemiluminescence in the presence of an oxidizable substrate and a source of peroxide. Specific pathogenic species can be detected by choosing the bacteriocin targeted for a particular species, or by choosing a specific capture reagent (e.g, antibody- or phage-mediated capture using magnetic microbeads) in combination with a broad spectrum bacteriocin (e.g., nisin).

Assays for diseased animals can be performed in a few hours. For example, bovine tuberculosis, caused by mycobacterial infection of cattle, currently requires a sixteen week period for a diagnosis. Using the present diagnostic methods, the presence of this disease can be determined in a few hours, for example, using the following procedure: A fecal or milk sample can be conveniently screened for the presence of mycobacteria by filtering the milk or fecal matter (suspended in buffer, e.g., phosphate buffered saline) through a 5 μm filter, which captures the clumps of waxy mycobacterial cells. Detection is then easily accomplished by labeling with a bacteriocin-metal complex, for example, a nisin-Co complex, and detecting chemiluminescence in the presence of an oxidizable substrate and a source of peroxide. Alternatively, the mycobacterial cells could be captured from the sample using a phage attached to microbeads which is specific for mycobacteria, and then the cells could be detected by labeling with a bacteriocin-metal complex and using chemiluminescence.

B. Diagnostic and Imaging Agents

The bacteriocin-metal complexes may be also used for diagnosis of disease. Bacteriocins of varying specificity for their target pathogens can be used for rapid identification of disease causing pathogens. A sample may be removed from a patient and tested using bacteriocin-metal complexes wherein the bacteriocin binds with specificity to a particular target species. For example, a sample of lung aspirate from a patient suffering from pneumonia can be tested using a battery of specific bacteriocin-metal complexes to determine the causative pathogen within a matter of minutes, instead of the usual hours required to grow the organism in culture for identification purposes. Bacteriocin-metal complexes of predetermined specificity for target organisms can be used distinguish between organisms contributing to dental plaque or other infection for purposes of choosing the appropriate treatment.

Diagnosis can also be accomplished via imaging of infected tissues using the complexes. Bacteriocin-metal complexes can be used to diagnose the pathogen present at sites of infections of the skin or mucosa. For example, *Streptococcus mutans* is the species most commonly associated with dental caries in humans. Bacteriocin-metal complexes can be used to visualize sites of colonization or infection on the gums or on an inflamed tooth by *S. mutans*. Tissue sections under microscopy can be examined for local chemiluminescence produced by bacteriocin-metal complexes binding to a site of infection. For example, mycobacteria can be visualized in a tissue sample and used to diagnose the causative agent of a disease condition.

Imaging can also be performed using the bacteriocin-metal complexes as magnetic resonance imaging agents. Paramagnetic metals alter the magnetic field in their vicinity such that paramagnetic metals can be easily imaged within a patient's body using magnetic resonance imaging. By using a paramagnetic metal in the bacteriocin-metal complexes, these metals can be targeted to the location of a site of infection within the body of a patient. Gadolinium is a preferred metal useful for magnetic resonance imaging because of its extremely high nuclear spin, which produces a very strong perturbation in the homogeneity of an applied magnetic field. For imaging the presence of pathogenic bacteria, for example, the Gd-bacteriocin chelated complex could be utilized with a bacteriocin specific for a particular pathogen.

Alternatively, by forming the bacteriocin-metal complex with a radioactive metal, preferably having a short half-life, the complex can be used as an agent in a medical tracer for gamma scintillography. For example, technicium 99, a short-lived radio-isotope, can be used in a bacteriocin-metal complex as a medical tracer for gamma scintillography and used for medical imaging, for example, a site of infection in a patient.

An imaging agent can also be prepared by cross-linking a bacteriocin to an anti-tumor monoclonal antibody using a hetero-bifunctional reagent, such as N-hydroxysuccinimide-activated N-propionylmaleimide. The malylated peptide antibiotic would then react with a native sulfhydryl on the antibody or a sulfhydryl introduced by treatment with a thiolating reagent such as iminothiolane. Once the peptide is grafted onto the antibody sidechain(s), a metal chelate of Gd or Tc, as discussed above, could be formed and used for imaging a site of a tumor in a patient. Additional heterobifunctional cross-linking agents are readily identified, for example, by referring to catalogs of reagents (e.g., the Pierce Chemical Co.).

C. Therapeutic Agents

The bacteriocin-metal complexes of the invention can be administered to a mammalian subject, including a human, as a therapeutic agent to treat a disease, condition or disorder that is known or hereinafter discovered to be responsive to the bacteriocin of the complex. Thus, the present invention encompasses methods for treating a patient who would benefit from administration of a particular bacteriocin by administering a therapeutically effective amount of a bacteriocin in the form of a metal-bacteriocin complex as described earlier herein. By "treatment" of a disease, condition or disorder is meant reduction in severity and/or frequency of symptoms, elimination of symptoms and/or underlying cause, prevention of the occurrence of symptoms and/or their underlying cause, and improvement or remediation of damage. Thus, "treating" a patient involves prevention of a particular disorder or adverse physiological event in a susceptible individual as well as treatment of a clinically symptomatic individual by inhibiting or causing regression of a disorder or disease. The therapeutically effective amount administered is a nontoxic but sufficient amount of the bacteriocin to provide the desired effect. As will be appreciated, the amount of a particular bacteriocin that is "effective" will vary from subject to subject, depending on the age, weight and general condition of the individual, the severity of the pathology being treated, the route of administration, the dosing regimen, the duration of treatment desired or necessary, and other factors known to the prescribing physician. Generally, a therapeutically effective amount is selected to provide a daily dosage in the range of about 0.001 and 10 mg/kg of body weight.

Accordingly, the invention includes pharmaceutical compositions comprising, as an active ingredient, at least one of the complexes of the invention in association with a pharmaceutical carrier or diluent. The composition can be administered by oral, parenteral (intramuscular, intraperitoneal, intravenous (IV) or subcutaneous) injection, transdermal (either passively or using iontophoresis or electroporation), topical or transmucosal (nasal, vaginal, rectal, or sublingual) routes of administration, or using bioerodible inserts, and can be formulated in dosage forms appropriate for each route of administration.

Particular bacteriocins with more or less specific binding to target pathogens may be used as therapeutic agents. Preferred complexes are comprised of nisin-cobalt complex, because of the low mammalian toxicity. Complexes of bacteriocin with radioactive transition or lanthanide metal (e.g., technicium ($^{99}$Tc)) may be useful therapeutic agents, and when attached to a monoclonal antibody or other delivery/carrier molecule also have potential as targeted therapeutic agents. For example, a bi-functional IgG molecule comprising an Fab fragment specific to a tumor antigen and an Fab fragment directed against nisin could be formed. These diagnostic and therapeutic uses have great promise in the fields of cancer and AIDS treatment.

D. Binding of Bacteriocin-Metal Complex to Target Organisms

The methods of the present invention are suitable for use in rapidly detecting gram positive bacteria and mycobacteria in samples as diverse as drinking water, hamburger and blood. The methods are also suitable for detecting gram negative bacteria, which have generally been permeabilized, although permeabilization is not always necessary, and for fungi when the fungal cell wall has been disrupted. For drinking water and low protein solutions, samples may be concentrated using thin film type-membranes so that captured bacterial cells can be resuspended in a smaller volume for easier analysis. More concentrated samples such as biological fluids and foodstuffs lend themselves to processing with rapid isolation techniques such as immuno-magnetic micro-beads, or high density immuno-silica micro-beads. Especially useful are micro-beads with covalently attached bacteriophage for targeting particular species of bacteria.

A core utility of the bacteriocin-metal complexes of the present invention is the binding activity specifically to viable bacteria. A preferred embodiment is a simple binding assay comprising labeling gram positive cells in suspension, pelleting the cells by centrifugation or isolating the cells by filtration or immuno-separation, washing unbound label, and detecting the bound complexes with chemiluminescent reagents. Bacterial cells are diluted from stock cultures and the cell suspensions are labeled at room temperature with a bacteriocin-metal complex at a concentration sufficient to achieve labeling. Generally a concentration of bacteriocin-metal complex of about 0.01 to 0.05 mg/mL is sufficient. The labeled cells can, optionally, be collected by centrifugation, filtration on micro-porous filters of the polycarbonate film type (Osmonics, Inc.) or rapid immuno-separation using antibody coated super para-magnetic particles. Phage coated paramagnetic particles may also be used. The labeled cells are then washed and resuspended in peptone water for assay with preferably, hydrogen peroxide/luminol or any number of oxidizable chemiluminescent substrates, including lucigenin, penicillin and the like.

Potential bacterial targets for the bacteriocin-metal complex of the present invention include, but are not limited to, pneumococci, streptococci, staphylococci, aerobic bacilli, anaerobic clostridia, listeria, nocardia, *Bacillus anthracis* (anthrax), Clostridial species (e.g. *C. botulinum* and *C. perfringes* whose exotoxins cause botulism and tetanus, respectively), *mycobacterium tuberculosis, mycobacterium avium, mycobacterium paratuberculosis, mycobacterium bovis* and *mycobacterium leprae*.

It is to be understood that while the invention has been described in conjunction with the preferred specific embodiments thereof, the foregoing description, as well as the examples which follow, are intended to illustrate and not limit the scope of the invention. Other aspects, advantages and modifications will be apparent to those skilled in the art to which the invention pertains.

All patents, patent documents, and publications cited herein are hereby incorporated by reference in their entirety.

Experimental

The following examples are put forth so as to provide those of ordinary skill in the art with a complete disclosure and description of how to make and use the bacteriocin-metal complexes disclosed and claimed herein, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Also, in these examples and throughout this specification, the abbreviations employed have their generally accepted meanings, as follows:

Å=Angstrom (0.1 nm)
C=Centigrade
kg=kilogram
M=Molar
mg=milligram
ml=milliliter
mm=millimeter
N=Normal
nm=nanometer
CFU=colony forming unit

EXAMPLE 1

Preparation of the Cobalt Complex of Nisin

Figure 3:
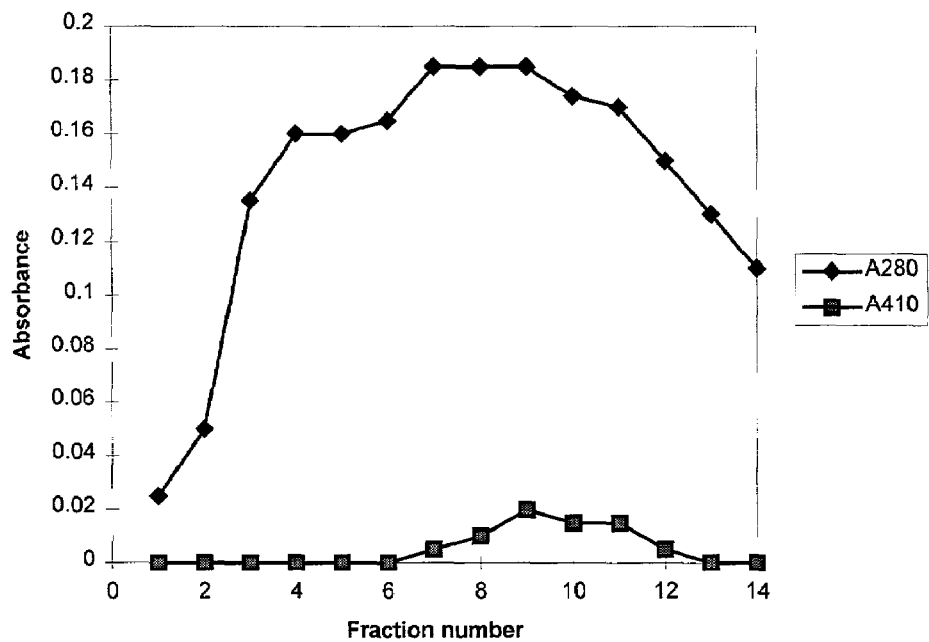
FIG. 3 is a chromatogram showing the G-25 Sephadex elution pattern of nisin-Co(II) complex, monitoring at 410 nm and 280 nm absorbance.

Nisin (Sigma 2.5% active material), 0.35 g, was dissolved in 8 mL of 1% (v/v) acetic acid. The solution was filtered through a pad of finely ground pumice stone to yield a clarified solution free of milk solids. The filtrate was treated with 0.072 g cobalt chloride to form the chelate. The complex was purified on a Sephadex G-25 column 2.5× 40 cm to remove inactive protein and unbound metal, as shown in FIG. 3. The fractions absorbing at 410 nm were pooled and freeze dried. The freeze dried powder was approximately 85% pure as judged by TLC on microcrystalline cellulose plates.

EXAMPLE 2

Demonstration of Binding of Complex to *Listeria Monocytogenes* Cells

Figure 4:
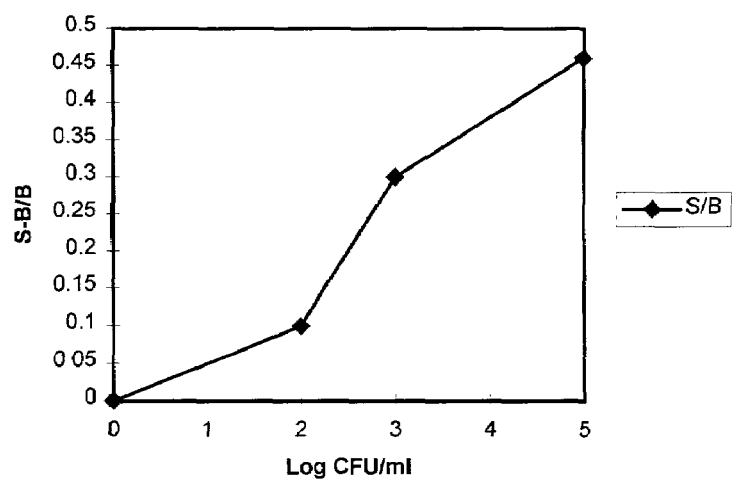
FIG. 4 is a graph of a chemiluminescent cell titration using Nisin-Co(II) showing luminescence relative to the number of *Listeria monocytogenes* cells.

Bacteria were diluted in sterile 0.1% peptone from cell concentrations of $10^7$ CFU/mL to 10 CFU/mL. The cells were treated with the Nisin-Co (II) complex (of example 4) at 30 μg/mL for twenty minutes at room temperature. The cells were centrifuged, rinsed with 0.5 mL peptone; centrifuged and re-suspended in 0.1 mL peptone. Chemiluminescence was measured using 0.2 mL of Luminol reagent purchased from NEN Life Sciences (Boston, Mass.) in a Luminator® luminometer. FIG. 4 shows the titration curve for the cells. From the data presented we estimate that the lowest detectable cell concentration to be approximately 10 to 100 cells per sample.

EXAMPLE 3

Demonstration of Binding of Nisin-Cobalt Complex

Figure 5:
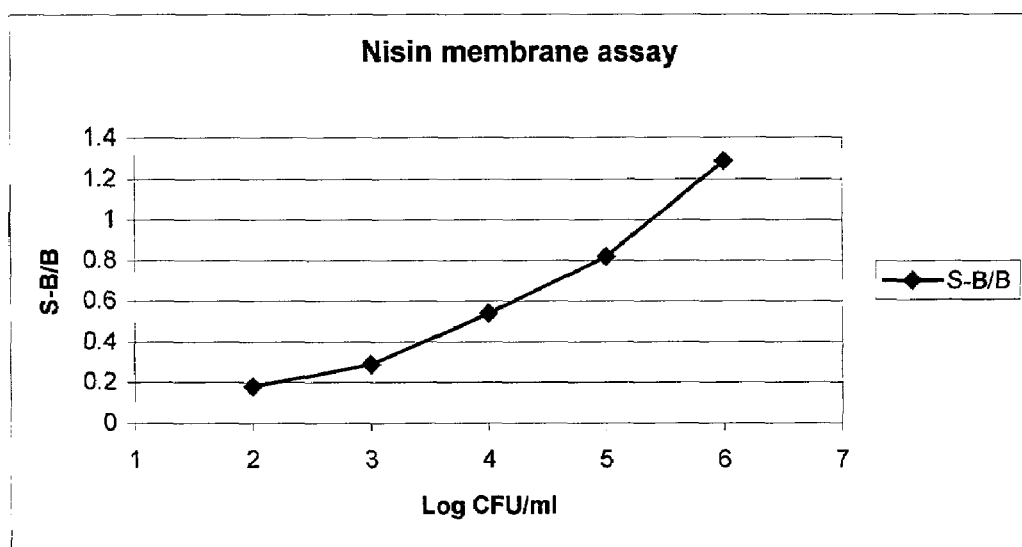
FIG. 5 is a graph illustrating the binding of nisin-cobalt complex to *Listeria monocytogenes* cells by membrane collection, as determined in Example 3.

The binding of nisin-cobalt complex to *Listeria monocytogenes* cells was demonstrated by membrane collection, as follows:

Bacteria were diluted in sterile 0.1% peptone from cell concentrations of $10^7$ CFU/mL to 10 CFU/mL. The cells were treated with the Nisin-Co (II) complex (of Example 1) at 30 μg/mL for twenty minutes at room temperature. The cells were collected by filtration on 0.2 μm polycarbonate track etch membrane (Osmonics), rinsed with 1.0 mL peptone; after which the membrane was transferred to 1.5 mL micro-centrifuge tube. Chemiluminescence was measured using 0.2 mL of Luminol reagent purchased from NEN Life Sciences (Boston, Mass.) in a Lum-T® luminometer. FIG. 5 shows the titration curve for the cells. From the data presented, the lowest detectable cell concentration is estimated to be about 100 cells per sample.

BIBLIOGRAPHY

1. Olsen, S., Mackinnon, L., Goulding, J., Bean, N. and Slutsker, L. Surveillance for Foodborne Disease Outbreaks—United States, 1993–1997. *CDC MMWR Surveillance Summary* 49 (SS01), 1–51 (2000).
2. Appelmelk, B. J. et al. Polymyxin B-Horseradish Peroxidase as tools in endotoxin research. *Anal. Biochem.* 207, 311–316 (1992).
3. Olstein, A. D. and Albert, R. A. U.S. Pat. No. 5,750,357. Method of rapid analyte detection.
4. Kricka, L. J. and Thorpe G. H. Chemiluminescent and bioluminescent methods in analytical chemistry. *Analyst* 108, 1274–1296 (1983).
5. Vaara, M., Vaara, M. T. Jensen, I., Helanderr, M., Nurminen, E. T. Reistchel and P. H. Makela. Characterization of the lipopolysaccharide from the polymyxin-resistant pmrA mutants of *Salmonella typhimurium*. *FEBS Lett.* 129, 145–149 (1981).
6. Sutcliffe, J., Tait-Kamradt, A., and Wondrack, L. *Streptococcus pneumoniae* and *Streptococcus pyogenes* resistant to macrolides but sensitive to clindamycin: a common resistance pattern mediated by an efflux system. *Antimicrob. Agents and Chemother.* 40, 1817–1824 (1996).
7. Gibreel, A. and Skold, O. High-level resistance to Trimethoprim in clinical isolates of *Campylobacter jejuni* by acquisition of foreign genes (dfr1 and dfr9) expressing drug-insensitive dihydrofolate reductases. *Antimicrob. Agent and Chemother.* 42, 3059–3064 (1998).
8. Williams, D. and Bardsley, B. The Vancomycin group of antibiotics and fight against resistant bacteria. *Angew. Che. Int. Ed.* 38, 1172–1193 (1999).
9. Nair, U., Chang, S., Armstrong, D. Rawjee, Y., Eggleston, D. and McArdle, J. Elucidation of Vancomycin's enantioselective binding site using its copper complex. *Chirality,* 8, 590–595 (1996).
10. Rost, M., Karge, E. and Klinger, W. What do we measure with Luminol-, Lucigenin-and Penicillin-amplified chemiluminescence? 1. Investigations with hydrogen peroxide and sodium hypochlorite. *J. Biolumin. Chemilumin.* 13, 355–363 (1998).
11. Pyle, B., Broadaway, S. and McFeters, G. Sensitive detection of *Escherichia coli* 0157:H7 in food and water by immunomagnetic separation and solid-phase laser cytometry. *Appl. Environ Microbiol.* 65, 1966–1972 (1999).
12. Restaino, L., Frampton, R., Irbe, M. and Allison, D. A 5-h screening and 24-h confirmation procedure for detecting Escherichia coli 0157:H7 in beef using direct epiflourescent microscopy and immunomagnetic separation. *Lett. Appl. Microbiol.* 24,401–404 (1997).
13. Sahl, H. G. and Bierbaum, G. Lantibiotics: Biosynthesis and Biological Activities of Uniquely Modified Peptides from Gram-Positive Bacteria. *Annu. Rev. Microbiol.* 52, 41–79(1998).
14. Bender, F. et al. *Gram-Negative Antibacterial Compositions.* U.S. Pat. No. 6,287,617.
15. Blackburn et al. *Nisin Compositions for Use As Enhanced, Broad Range Bactericides.* U.S. Pat. No. 5,691,301.

The invention claimed is:

1. An isolated chelated complex comprising:
   nisin, fusion proteins thereof, and mixtures thereof; and
   a detectable label comprising cobalt chelated with the nisin.

2. The complex of claim 1, wherein the complex binds to microbial cells selected from the group consisting of gram positive bacteria or mycobacteria.

3. The complex of claim 1, wherein the complex binds to gram negative bacteria or fungi.

4. A method for conducting a chemiluminescent assay of pathogens comprising:
   (a) contacting a sample with the complex of claim 1, under conditions and for a time sufficient to allow the complex to bind with pathogens present in the sample;
   (b) removing any unbound complex; and
   (c) detecting the pachogens by contacting the sample with a peroxide source and an oxidizable substrae.

5. The method of claim 4, wherein pathogens are isolated from the sample prior to contacting the sample with the complex.

6. The method of claim 5, wherein pathogens are isolated from the sample using antibody-attached microbeads or phage-attached microbeads.

7. The method of claim 6, wherein the microbeads comprise a magnetic matenal.

8. The method of claim 4, wherein the peroxide source is selected from the group consisting of hydrogen peroxide, benzoyl peroxide and cumyl peroxide.

9. The method of claim 4, wherein the oxidizable substrate is selected from the group consisting of luininol and its derivatives, lucigerain, penicillin, luciferin, and polyaromatic phthalylhydrazides.

10. The method of claim 4, wherein the pathogens are grain positive bacteria or mycobacteria.

11. The method of claim 4, wherein the patbogeas are gram negative bacteria or fungi.

12. The method of claim 4, wherein the bacteria are selected from the group consisting of *lactococci, leuconostocs, micrococci, pediococci, actisomyces, mycoabacteria, pneuniococci, streptococci, staphylococci, aerobic bacilli, anaerobic clostridia, listeria* and *nocardia*.

13. The method of claim 12, wherein the mycobacteria are selected from the group consisting of *mycobacteriurn tuberculosis, inycobacterium avium, mnycobacterium paratuberculosis, mycobacterium bovis* and *mycobacterium leprae*.

14. The method of claim 12, wherein the bacteria are selected from the group consisting of *Bacillus ntliracis, Clostridinin botulinum* and *Clostridium perfringes*.

* * * * *

SEQUENCE LISTING

<160> NUMBER OF SEQ ID NOS: 8

<210> SEQ ID NO 1
<211> LENGTH: 52
<212> TYPE: PRT
<213> ORGANISM: Staphylococcus gallinarum

<400> SEQUENCE: 1

Met Glu Ala Val Lys Glu Lys Asn Glu Leu Phe Asp Leu Asp Val Lys
1               5                   10                  15

Val Asn Ala Lys Glu Ser Asn Asp Ser Gly Ala Glu Pro Arg Ile Ala
            20                  25                  30

Ser Lys Phe Leu Cys Thr Pro Gly Cys Ala Lys Thr Gly Ser Phe Asn
        35                  40                  45

Ser Tyr Cys Cys
    50

<210> SEQ ID NO 2
<211> LENGTH: 60
<212> TYPE: PRT
<213> ORGANISM: Staphylococcus epidermidis

<400> SEQUENCE: 2

Met Lys Asn Asn Lys Asn Leu Phe Asp Leu Glu Ile Lys Lys Glu Thr
1               5                   10                  15

Ser Gln Asn Thr Asp Glu Leu Glu Pro Gln Thr Ala Gly Pro Ala Ile
            20                  25                  30

Arg Ala Ser Val Lys Gln Cys Gln Lys Thr Leu Lys Ala Thr Arg Leu
        35                  40                  45

Phe Thr Val Ser Cys Lys Gly Lys Asn Gly Cys Lys
    50                  55                  60

<210> SEQ ID NO 3
<211> LENGTH: 22
<212> TYPE: PRT
<213> ORGANISM: Streptococcus mutans

<400> SEQUENCE: 3

Phe Lys Ser Trp Ser Phe Cys Thr Pro Gly Cys Ala Lys Thr Gly Ser
1               5                   10                  15

Phe Asn Ser Tyr Cys Cys
            20

<210> SEQ ID NO 4
<211> LENGTH: 56
<212> TYPE: PRT
<213> ORGANISM: Bacillus subtilis

<400> SEQUENCE: 4

Met Ser Lys Phe Asp Asp Phe Asp Leu Asp Val Val Lys Val Ser Lys
1               5                   10                  15

Gln Asp Ser Lys Ile Thr Pro Gln Trp Lys Ser Glu Ser Leu Cys Thr
            20                  25                  30

Pro Gly Cys Val Thr Gly Ala Leu Gln Thr Cys Phe Leu Gln Thr Leu
        35                  40                  45

Thr Cys Asn Cys Lys Ile Ser Lys
    50                  55

<210> SEQ ID NO 5
<211> LENGTH: 57
<212> TYPE: PRT
<213> ORGANISM: Lactococcus lactis

<400> SEQUENCE: 5

```
Met Ser Thr Lys Asp Phe Asn Leu Asp Leu Val Ser Val Ser Lys Lys
 1               5                  10                  15
Asp Ser Gly Ala Ser Pro Arg Ile Thr Ser Thr Ser Leu Cys Thr Pro
            20                  25                  30
Gly Cys Lys Thr Gly Ala Leu Met Gly Cys Asn Met Lys Thr Ala Thr
        35                  40                  45
Cys His Cys Ser Ile His Val Ser Lys
    50                  55
```

<210> SEQ ID NO 6
<211> LENGTH: 52
<212> TYPE: PRT
<213> ORGANISM: Staphylococcus epidermidis

<400> SEQUENCE: 6

```
Met Glu Ala Val Lys Glu Lys Asn Asp Leu Phe Asn Leu Asp Val Lys
 1               5                  10                  15
Val Asn Ala Lys Glu Ser Asn Asp Ser Gly Ala Glu Pro Arg Ile Ala
            20                  25                  30
Ser Lys Phe Ile Cys Thr Pro Gly Cys Ala Lys Thr Gly Ser Phe Asn
        35                  40                  45
Ser Tyr Cys Cys
    50
```

<210> SEQ ID NO 7
<211> LENGTH: 55
<212> TYPE: PRT
<213> ORGANISM: Staphylococcus epidermidis

<400> SEQUENCE: 7

```
Met Asn Asn Ser Leu Phe Asp Leu Asn Leu Asn Lys Gly Val Glu Thr
 1               5                  10                  15
Gln Lys Ser Asp Leu Ser Pro Gln Ser Ala Ser Val Leu Lys Thr Ser
            20                  25                  30
Ile Lys Val Ser Lys Lys Tyr Cys Lys Gly Val Thr Leu Thr Cys Gly
        35                  40                  45
Cys Asn Ile Thr Gly Gly Lys
    50                  55
```

<210> SEQ ID NO 8
<211> LENGTH: 767
<212> TYPE: DNA
<213> ORGANISM: Streptococcus lactis

<400> SEQUENCE: 8

```
agttgacgaa tatttaataa ttttattaat atcttgattt tctagttcct gaataatata      60
gagataggtt tattgagtct tagacatact tgaatgacct agtcttataa ctatactgac    120
aatagaaaca ttaacaaatc taaaacagtc ttaattctat cttgagaaag tattggtaat    180
aatattattg tcgataacgc gagcataata aacggctctg attaaattct gaagtttgtt    240
agatacaatg atttcgttcg aaggaactac aaaataaatt ataaggaggc actcaaaatg    300
agtacaaaag attttaactt ggatttggta tctgtttcga agaaagattc aggtgcatca    360
```

```
                                      -continued
ccacgcatta caagtatttc gctatgtaca cccggttgta aaacaggagc tctgatgggt    420
tgtaacatga aaacagcaac ttgtcattgt agtattcacg taagcaaata accaaatcaa    480
aggatagtat tttgttagtt cagacatgga tactatccta tttttataag ttatttaggg    540
ttgctaaata gcttataaaa ataaagagag gaaaaaacat gataaaaagt tcatttaaag    600
ctcaaccgtt tttagtaaga aatacaattt tatctccaaa cgataaacgg agttttactg    660
aatatactca agtcattgag actgtaagta aaaataaagt tttttggaa cagttactac     720 tagctaatcc taaactctat gatgttatgc agaaatataa tgctggt                  767
```